US012758282B1

(12) United States Patent
Gendreau

(10) Patent No.: US 12,758,282 B1
(45) Date of Patent: Oct. 13, 2026

(54) SLIM IMPLANT DEVICE FOR A TIBIAL PLATEAU LEVELING OSTEOTOMY

(71) Applicant: The TPLO Company LLC, Carson City, NV (US)

(72) Inventor: Claude Luc Gendreau, Highland, IN (US)

(73) Assignee: The TPLO Company LLC, Carson City, NV (US)

( * ) Notice: Subject to any disclaimer, the term of this patent is extended or adjusted under 35 U.S.C. 154(b) by 0 days.

(21) Appl. No.: 19/529,753

(22) Filed: Feb. 4, 2026

(51) Int. Cl.
*A61B 17/80* (2006.01)
*A61B 17/86* (2006.01)

(52) U.S. Cl.
CPC .......... *A61B 17/8061* (2013.01); *A61B 17/86* (2013.01); *A61B 2503/40* (2013.01)

(58) Field of Classification Search
CPC ........................ A61B 17/8061; A61B 17/8095
See application file for complete search history.

(56) References Cited

U.S. PATENT DOCUMENTS

| | | | |
|---|---|---|---|
| 4,677,973 | A | 7/1987 | Slocum |
| 4,762,122 | A | 8/1988 | Slocum |
| 4,800,874 | A | 1/1989 | David |
| 4,867,144 | A | 9/1989 | Karas |
| 4,988,350 | A | 1/1991 | Herzberg |
| 5,304,180 | A | 4/1994 | Slocum |
| 5,749,872 | A | 5/1998 | Kyle |
| 5,868,749 | A | 2/1999 | Reed |

(Continued)

FOREIGN PATENT DOCUMENTS

| | | | |
|---|---|---|---|
| AU | 2023222926 | A1 | 3/2024 |
| CN | 201586060 | U | 9/2010 |

(Continued)

OTHER PUBLICATIONS

Macdonald, Rachel, et al., "A synthetic bone insert may protect the lateral cortex and fixation plate following a high tibial osteotomy by reducing the tensile strains", European Society of Sports Traumatology, Knee Surgery, Arthroscopy, published Jul. 3, 2019, pp. 1814-1820, vol. 28, No. 6, Springer International, Berlin, Germany.

(Continued)

*Primary Examiner* — Andrew Yang
(74) *Attorney, Agent, or Firm* — MILLER, CANFIELD, PADDOCK AND STONE; Gregory A. Lewis

(57) ABSTRACT

An implant device made of an implant grade alloy that includes: an epiphyseal tibial plate section comprising at least three screw holes; a metaphyseal tibial plate section comprising at least three screw holes; and a ligament joining the tibial plate sections that spans a curvilinear tibial cut. The epiphyseal tibial plate section comprises a curvilinear and proximal portion, the curvilinear portion oriented perpendicular to the ligament and comprising a cut-adjacent curvilinear surface, and the proximal portion is perpendicular and extending proximally to the curvilinear portion. The metaphyseal tibial plate section comprises an elongated distal and cranial portion, the cranial portion oriented cranially to the distal portion and perpendicular to the ligament, and the distal portion extending distally from the cranial portion. The widths of the ligament and the proximal portion are greater than the width of each of the curvilinear portion, the elongated distal portion and the cranial portion.

20 Claims, 10 Drawing Sheets

(56) References Cited

U.S. PATENT DOCUMENTS

| | | | |
|---|---|---|---|
| 5,904,684 | A | 5/1999 | Rooks |
| 6,077,266 | A | 6/2000 | Medoff |
| 6,096,040 | A | 8/2000 | Esser |
| 6,623,486 | B1 | 9/2003 | Weaver |
| 6,902,567 | B2 | 6/2005 | Del Medico |
| 7,090,676 | B2 | 8/2006 | Huebner |
| 7,189,237 | B2 | 3/2007 | Huebner |
| 7,267,678 | B2 | 9/2007 | Medoff |
| 7,951,178 | B2 | 5/2011 | Jensen |
| 8,177,818 | B2 | 5/2012 | Wotton, III |
| 8,523,921 | B2 | 9/2013 | Horan |
| 8,753,343 | B2 | 6/2014 | Staeubli |
| 9,271,773 | B2 | 3/2016 | Hwa et al. |
| 10,258,396 | B2 | 4/2019 | Kanzanovicz |
| 10,299,841 | B2 | 5/2019 | Dunlop |
| 10,864,026 | B2 | 12/2020 | Wotton, III |
| 11,026,728 | B2 | 6/2021 | Horan |
| 11,096,729 | B2 | 8/2021 | Dunlop |
| 11,123,119 | B2 | 9/2021 | Dunlop |
| 11,207,112 | B2 | 12/2021 | Dunlop |
| 11,298,167 | B2 | 4/2022 | Dunlop |
| 11,317,953 | B2 | 5/2022 | Dunlop |
| 11,337,740 | B2 | 5/2022 | Silva |
| 11,357,553 | B2 | 6/2022 | Paton |
| 11,419,648 | B2 | 8/2022 | Dunlop |
| 2002/0156474 | A1 | 10/2002 | Wack |
| 2004/0116930 | A1 | 6/2004 | O'Driscoll |
| 2004/0193165 | A1 | 9/2004 | Orbay |
| 2004/0225291 | A1 | 11/2004 | Schwammberger |
| 2005/0010226 | A1 | 1/2005 | Grady |
| 2005/0015089 | A1 | 1/2005 | Young |
| 2005/0216008 | A1 | 9/2005 | Zwirnmann et al. |
| 2005/0240187 | A1 | 10/2005 | Huebner |
| 2006/0009771 | A1 | 1/2006 | Orbay |
| 2006/0149275 | A1 | 7/2006 | Cadmus |
| 2006/0173458 | A1 | 8/2006 | Forstein |
| 2006/0229621 | A1 | 10/2006 | Cadmus |
| 2007/0083204 | A1 | 4/2007 | Sidebotham |
| 2010/0152783 | A1 | 6/2010 | Borostyankoi |
| 2011/0093018 | A1 | 4/2011 | Prasad |
| 2013/0090694 | A1 | 4/2013 | Norris |
| 2015/0127011 | A1 | 5/2015 | Dunlop et al. |
| 2019/0358039 | A1 | 11/2019 | Ducharme |
| 2019/0374266 | A1 | 12/2019 | Paton |
| 2020/0253653 | A1 | 8/2020 | Wotton, III |
| 2021/0052311 | A1 | 2/2021 | Fitch et al. |
| 2021/0085380 | A1 | 3/2021 | Daye |
| 2021/0212738 | A1 | 7/2021 | Daye |
| 2021/0298806 | A2 | 9/2021 | Daye |
| 2021/0338293 | A1 | 11/2021 | Silva |
| 2021/0361331 | A1 | 11/2021 | Daye |
| 2022/0338909 | A1 | 10/2022 | Dunlop |
| 2024/0058042 | A1 | 2/2024 | Damron |

FOREIGN PATENT DOCUMENTS

| | | | |
|---|---|---|---|
| DE | 10015734 | A1 | 9/2001 |
| EP | 2937051 | A1 | 4/2014 |
| FR | 2405062 | A1 | 5/1979 |
| FR | 2405705 | A1 | 5/1979 |
| FR | 2406429 | A1 | 5/1979 |
| FR | 2887433 | B1 | 9/2007 |
| KR | 102313246 | B1 | 10/2021 |
| TW | M525169 | U | 7/2016 |
| WO | 200119267 | A1 | 3/2001 |
| WO | 2003013623 | A1 | 2/2003 |
| WO | 2004024009 | A1 | 3/2004 |
| WO | 2005048888 | A1 | 6/2005 |
| WO | 2007137437 | A2 | 12/2007 |
| WO | 2022204552 | A1 | 9/2022 |

OTHER PUBLICATIONS

International Searching Authority, "International Search Report and the Written Opinion", International Patent Application No. PCT/US2026/010413, Apr. 22, 2026, 15 pages.

Veterinary Orthopedic Implants, Inc., "Catalog 2019", pp. i-iii, 2.12-2.17, 5.3-5.4, 5.9-6.25, and 10.8.

Veterinary Orthopedic Implants, Inc., "Catalog 2021-2022", pp. i-v, and 1.10-1.22.

Veterinary Orthopedic Implants, Inc., "Product Catalog 2023", 2023, pp. i-iii, and 10-18.

Kyon AG, "Product Catalog 2023", 2023, pp. i-iii, and 39-42.

Movora LLC, "Product Catalog 2023", 2023, pp. i-vii, 27-29, 156-157, and 241-249.

Dallago, M., et al., "Effect of Plate Type on Tibial Plateau Levelling and Medialization Osteotomy for Treatment of Cranial Cruciate Ligament Rupture and Concomitant Medial Patellar Luxation in Small Breed Dogs: An In Vitro Study", Vet. Comp. Orthop. Traumatol., published May 2, 2023, 36(04), pp. 212-217, Georg Thieme Verlag KG, Stuttgart, Germany.

Animal Surgical Center of Michigan, "Tibial Plateau Leveling Osteotomy—TPLO", available at https://www.animalsurgicalcenter.com/tibial-plateau-leveling-osteotomy-tplo, accessed Apr. 10, 2024.

SLIM IMPLANT DEVICE FOR A TIBIAL PLATEAU LEVELING OSTEOTOMY

FIELD OF THE DISCLOSURE

The present disclosure relates to a surgical implant device used as part of a tibial plateau leveling osteotomy (TPLO) procedure and, more specifically, a slim implant device for an animal (e.g., a canine) undergoing a tibial plateau leveling osteotomy (TPLO) procedure that reduces incision size, procedure duration, the risk of infection, and provides a more secure fixation.

BACKGROUND

As is well known in the field, the cranial cruciate ligament (CCL) in many animals can partially rupture, fully rupture, or otherwise degenerate over time. The CCL provides stability to the stifle joint of an animal by preventing backward movement of the femur relative to the tibia. Some dogs, cats and possible other species of animals can develop an exaggerated backward slope of the upper surface (plateau) of their tibia bones. This slope contributes to stress on the CCL ligament, often leading to its rupture or degeneration. Once the CCL ligament is compromised, the animal experiences pain, and arthritis can quickly develop in the stifle joint.

Various TPLO implant devices are known in the field to stabilize the bone fragments in their new position following an osteotomy. During a typical TPLO procedure, a veterinary surgeon will make a curvilinear cut within the tibia that is relatively close to the tibial plateau and stifle joint, and separate metaphyseal and epiphyseal sections of the tibial bone. After the curvilinear cut to the tibia is completed, the surgeon then rotates the tibial plateau of the epiphyseal section relative to the metaphyseal section to an optimal angle to reduce stress on the CCL ligament in the stifle joint. An implant device is then used to secure the new orientation of the epiphyseal section relative to the metaphyseal section of the tibial bone with the plate of the device attached to each bone section. The implant device is left in the animal after the TPLO procedure until the osteotomy is healed or indefinitely if there is no rejection of the implant and no infection.

The conventional implant devices employed in TPLO procedures have several disadvantages and problems. Most such implant devices employ a plate with a substantially elongated appendage affixed to the distal section of the tibia, ostensibly to ensure that the plate is adequately secured to this portion of the tibia. However, the substantial length of the appendage of these implant devices necessitates a long surgical exposure, which can extend recovery times and lead to an increased likelihood of infection and implant rejection.

Accordingly, there is a need for an implant device design for TPLO procedures that reduces incision size, the duration of the procedure, and the risk of post-surgery implant reaction, infection, and other complications. Such a device should also provide a more uniform securement of the epiphyseal and metaphyseal fragments separated by the curvilinear cut between the two tibial sections during and after recovery.

SUMMARY

According to an aspect of the disclosure, an implant device for a tibial plateau leveling osteotomy is provided that includes: an epiphyseal tibial plate section comprising at least three screw holes, a bone-contacting surface and an upper surface, each screw hole running between the bone-contacting and upper surfaces and configured to accept a bone screw to secure the epiphyseal plate section to an epiphyseal tibial bone fragment; a metaphyseal tibial plate section comprising at least three screw holes, a bone-contacting surface and an upper surface, each screw hole running between the bone-contacting and upper surfaces and configured to accept a bone screw to secure the metaphyseal plate section to a metaphyseal tibial bone fragment; and a ligament joining the tibial plate sections and configured to span a curvilinear tibial cut from a tibial plateau leveling osteotomy, wherein the curvilinear cut separates the epiphyseal and metaphyseal tibial bone fragments. Each of the metaphyseal and epiphyseal tibial plate sections and the ligament comprises an implant grade alloy. The epiphyseal tibial plate section comprises a curvilinear portion and a proximal portion, the curvilinear portion oriented perpendicular to the ligament and comprising a cut-adjacent curvilinear surface configured to be positioned adjacent to the curvilinear cut, and the proximal portion is perpendicular and extending proximally to the curvilinear portion. The metaphyseal tibial plate section comprises an elongated distal portion and a cranial portion, the cranial portion oriented cranially to the distal portion and perpendicular to the ligament, and the distal portion extending distally from the cranial portion. Further, each of the tibial plate sections and the ligament comprises a width that is substantially uniform, and each of the width of the ligament and a width of the proximal portion is greater than a width of each of the curvilinear portion, the elongated distal portion and the cranial portion.

According to an aspect of the disclosure, an implant device for a tibial plateau leveling osteotomy is provided that includes: an epiphyseal tibial plate section comprising at least three screw holes, a bone-contacting surface and an upper surface, each screw hole running between the bone-contacting and upper surfaces and configured to accept a bone screw to secure the epiphyseal plate section to an epiphyseal tibial bone fragment; a metaphyseal tibial plate section comprising at least three screw holes, a bone-contacting surface and an upper surface, each screw hole running between the bone-contacting and upper surfaces and configured to accept a bone screw to secure the metaphyseal plate section to a metaphyseal tibial bone fragment; and a ligament joining the tibial plate sections and configured to span a curvilinear tibial cut from a tibial plateau leveling osteotomy, wherein the curvilinear cut separates the epiphyseal and metaphyseal tibial bone fragments. Each of the metaphyseal and epiphyseal tibial plate sections and the ligament comprises an implant grade alloy. The epiphyseal tibial plate section comprises a curvilinear portion and a proximal portion, the curvilinear portion oriented perpendicular to the ligament and comprising a cut-adjacent curvilinear surface configured to be positioned adjacent to the curvilinear cut, and the proximal portion is perpendicular and extending proximally to the curvilinear portion. Further, the metaphyseal tibial plate section comprises an elongated distal portion and a cranial portion, the cranial portion comprising a cut-adjacent curvilinear surface configured to be positioned adjacent to the curvilinear cut and oriented cranially relative to the distal portion and perpendicular to the ligament, and the distal portion extending distally from the cranial portion. In addition, each of the tibial plate sections and the ligament comprises a width that is substantially uniform, and each of the width of the ligament and a width of the proximal portion is greater than a width of each of the curvilinear portion, the elongated distal portion and the cranial portion.

According to an aspect of the disclosure, an implant device for a tibial plateau leveling osteotomy is provided that includes: an epiphyseal tibial plate section comprising at least three screw holes, a bone-contacting surface and an upper surface, each screw hole running between the bone-contacting and upper surfaces and configured to accept a bone screw to secure the epiphyseal plate section to an epiphyseal tibial bone fragment; a metaphyseal tibial plate section comprising at least three screw holes, a bone-contacting surface and an upper surface, each screw hole running between the bone-contacting and upper surfaces and configured to accept a bone screw to secure the metaphyseal plate section to a metaphyseal tibial bone fragment; and a ligament joining the tibial plate sections and configured to span a curvilinear tibial cut from a tibial plateau leveling osteotomy, wherein the curvilinear cut separates the epiphyseal and metaphyseal tibial bone fragments. Each of the metaphyseal and epiphyseal tibial plate sections and the ligament comprises an implant grade alloy. The epiphyseal tibial plate section comprises a curvilinear portion and a proximal portion, the curvilinear portion oriented perpendicular to the ligament and comprising a cut-adjacent curvilinear surface configured to be positioned adjacent to the curvilinear cut, and the proximal portion is perpendicular and extending proximally to the curvilinear portion. The metaphyseal tibial plate section comprises an elongated distal portion and a cranial portion, the cranial portion comprising a cut-adjacent curvilinear surface configured to be positioned adjacent to the curvilinear cut and oriented cranially to the distal portion and perpendicular to the ligament, and the distal portion extending distally from the cranial portion. Further, each of the tibial plate sections and the ligament comprises a width that is substantially uniform, and each of the width of the ligament and a width of the proximal portion is greater than a width of each of the curvilinear portion, the elongated distal portion and the cranial portion. In addition, the cranial portion of the metaphyseal tibial plate section has at least two screw holes and comprises a metaphyseal cranial segment extending cranially and perpendicular to the ligament and a metaphyseal caudal segment extending caudally and perpendicular to the ligament.

Additional features and advantages will be set forth in the detailed description which follows, and in part will be readily apparent to those skilled in the art from that description or recognized by practicing the embodiments as described herein, including the detailed description which follows, the claims, as well as the appended drawings.

BRIEF DESCRIPTION OF THE DRAWINGS

It is to be understood that both the foregoing general description and the following detailed description are merely exemplary, and are intended to provide an overview or framework to understanding the nature and character of the claims. The accompanying drawings are included to provide a further understanding, and are incorporated in and constitute a part of this specification. The drawings illustrate one or more embodiments, and together with the description serve to explain principles and operation of the various embodiments, wherein:

DETAILED DESCRIPTION

Figure 1A:
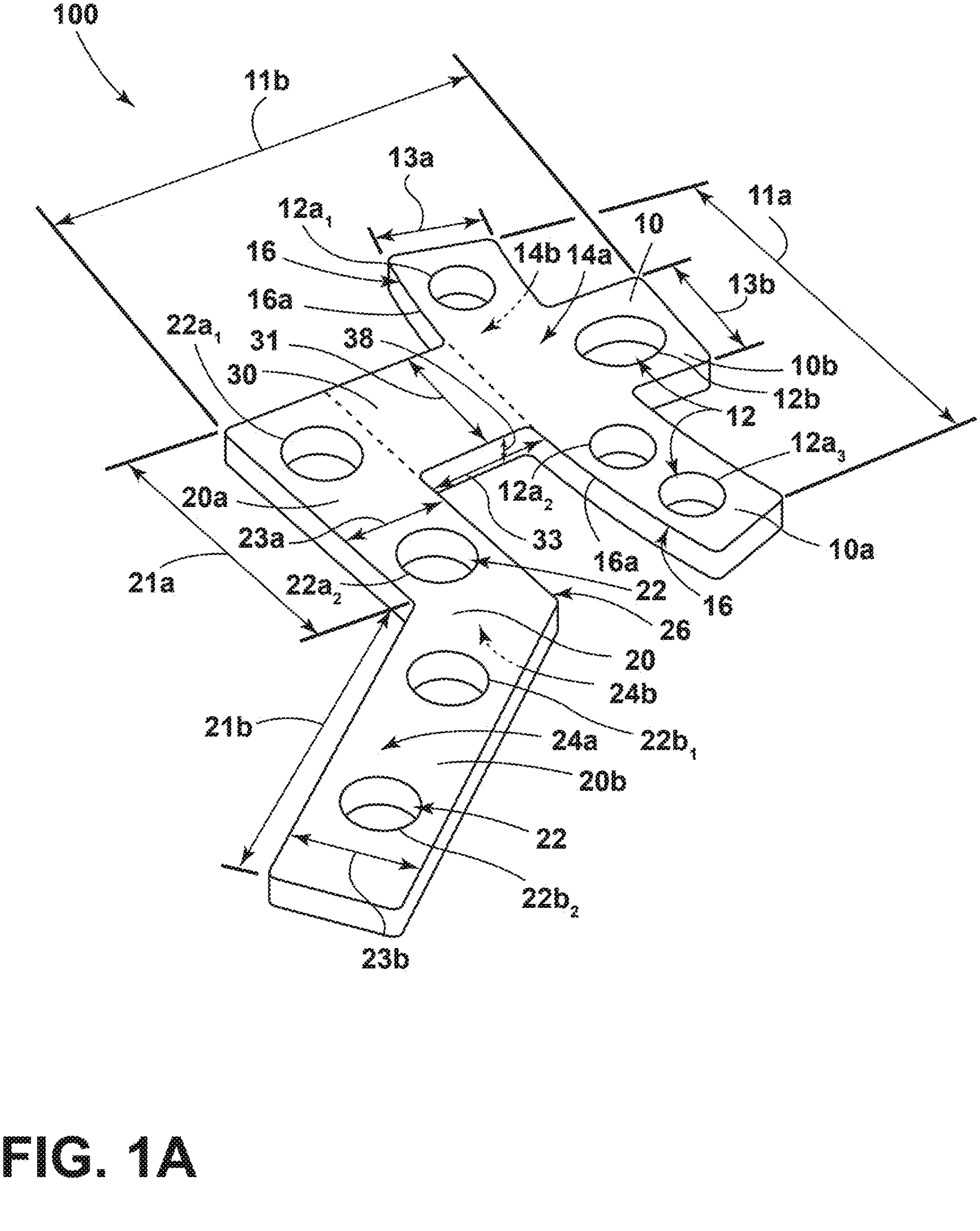
FIG. 1A is a perspective view of an implant device with epiphyseal and metaphyseal tibial plate sections and a ligament, according to an embodiment of the disclosure.

In the following detailed description, for purposes of explanation and not limitation, example embodiments disclosing specific details are set forth to provide a thorough understanding of various principles of the present disclosure. However, it will be apparent to one having ordinary skill in the art, having had the benefit of the present disclosure, that the present disclosure may be practiced in other embodiments that depart from the specific details disclosed herein. Moreover, descriptions of well-known devices, methods and materials may be omitted so as not to obscure the description of various principles of the present disclosure. Finally, wherever applicable, like reference numerals refer to like elements.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Directional terms as used herein—for example "up," "down," "right," "left," "front," "back," "top," "bottom"—are made only with reference to the figures as drawn and are not intended to imply absolute orientation.

Unless otherwise expressly stated, it is in no way intended that any method set forth herein be construed as requiring that its steps be performed in a specific order. Accordingly, where a method claim does not actually recite an order to be followed by its steps, or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow;

plain meaning derived from grammatical organization or punctuation; and the number or type of embodiments described in the specification.

As used herein, the singular forms "a," "an" and "the" include plural referents unless the context clearly dictates otherwise. Thus, for example, reference to a "component" includes aspects having two or more such components, unless the context clearly indicates otherwise.

As used herein, the "caudal" direction (see FIG. 1B and corresponding description) refers to aspects of the implant devices of the disclosure that point toward the caudal direction of the animal with the device, as implanted, i.e., a direction generally toward the tail of the animal.

As used herein, the "cranial" direction (see FIG. 1B and corresponding description) refers to aspects of the implant devices of the disclosure that point toward the cranial direction of the animal with the device, as implanted, i.e., a direction generally toward the head of the animal.

As used herein, the "proximal" direction (see FIG. 1B and corresponding description) refers to aspects of the implant devices of the disclosure that point toward a proximal direction within the leg of the animal with the device, as implanted, i.e., a direction generally toward the tibial plateau and/or stifle joint of the animal.

As used herein, the "distal" direction (see FIG. 1B and corresponding description) refers to aspects of the implant devices of the disclosure that point toward a distal direction within the leg of the animal with the device, as implanted, i.e., a direction generally away from the tibial plateau and/or stifle joint of the animal toward its paw, pes or foot.

As also used herein, the term "substantially uniform", as used in connection with the width of one or more plate sections of the implant device of the disclosure, means that the width does not vary substantially along the length of the plate section. More specifically, a "substantially uniform" width of the plate section cannot vary by more than 100% of the width of the plate section at any one location along the length of the plate section.

The present disclosure is generally directed to slim implant device designs for TPLO procedures that reduce incision size, procedure duration, and the risk of post-surgery reaction, infection, and other complications. According to a typical TPLO procedure, a veterinary surgeon will make a curvilinear cut within the tibia, relatively close to the tibial plateau and stifle joint, and separate metaphyseal and epiphyseal sections of the tibial bone. The slim implant device designs of the disclosure are configured to facilitate an effective, uniform and particularly strong securement of the curvilinear cut (i.e., as formed by the TPLO procedure) between the tibial sections during and after recovery of the animal (e.g., a canine) while also being relatively easy to implant with a short implantation procedure.

Tibial plateau osteotomy implant devices of the disclosure comprise, or consist essentially of, an epiphyseal tibial plate section, a metaphyseal tibial plate section, and a ligament configured to join the tibial plate sections, with each of the plate sections and ligament comprising an implant grade alloy and the ligament configured to span a curvilinear tibial cut from a tibial plateau leveling osteotomy. The curvilinear cut separates epiphyseal and metaphyseal tibial bone fragments that result from the osteotomy. Each of the plate sections includes at least three screw holes, each screw hole configured to accept a bone screw to secure the respective plate section to the respective epiphyseal or metaphyseal tibial bone fragment. Further, the epiphyseal plate section includes a curvilinear portion and a proximal portion, and the metaphyseal plate section includes an elongated distal portion and a cranial portion. A cut-adjacent curvilinear surface of the curvilinear portion is configured to be aligned with the curvilinear cut and generally has the same shape as the curvilinear cut. In addition, the width of each of the tibial plate sections and the ligament is substantially uniform with the width of the ligament and proximal portion being greater than the width of each of the curvilinear portion, the elongated distal portion and the cranial portion.

The implant devices of the disclosure offer several advantages over conventional implant devices employed in TPLO procedures. The implant device configurations of the disclosure are slim with a relatively short elongated distal portion, which facilitates relatively shorter incision sizes, shorter duration operations, lower implant reaction risk, lower infection risk, and lower risk of implant device rejection. Further, the implant device configurations of the disclosure are readily adaptable for TPLO procedures employed on animals of varying sizes (e.g., different dog breeds). In addition, the implant devices of the disclosure, as configured with a curvilinear portion, are expected to distribute stress more uniformly across the curvilinear cut to the tibia from the TPLO procedure.

Referring now to FIGS. 1A-1E, an implant device 100 for a TPLO procedure is depicted (see also FIGS. 2A-2C and corresponding description further below, showing the device 100 and screws 180, collectively implanted as implant assembly 200). The implant device 100 shown in FIGS. 1A-1E includes an epiphyseal tibial plate section 10 with at least three screw holes 12, an exterior surface 14*a*, and a bone-contacting surface 14*b*. Unless otherwise noted, each screw hole 12 of the epiphyseal tibial plate section 10 has a round shape and is configured to accept a bone screw 180 to secure the plate section 10 to the epiphyseal tibial bone fragment 110 (see FIGS. 2A-2C). In some implementations of the implant device 100, one screw hole 12*b* (e.g., the proximal-most screw hole) of the epiphyseal tibial plate section 10 can be elongated in a direction perpendicular to a curvilinear cut 150 of the tibial bone (e.g., in the proximal direction), as shown in exemplary form in FIGS. 1A-1E. In other embodiments, the screw hole 12*b* is round (not shown). In general, the epiphyseal tibial plate section 10 is configured to attach to an epiphyseal tibial bone fragment 110 that results from the TPLO procedure and, particularly, from a curvilinear cut 150 to a tibial bone. The epiphyseal tibial plate section 10 also functions to distribute stress (e.g., from movement of the tibia and stifle joint associated with movement by the animal) uniformly across a curvilinear tibial cut 150.

Referring again to the implant device 100, as depicted in exemplary form in FIGS. 1A-1E, the epiphyseal tibial plate section 10 includes a curvilinear portion 10*a*. In embodiments, the curvilinear portion 10*a* is oriented perpendicular to the ligament 30. In some implementations, the curvilinear portion 10*a* is oriented substantially perpendicular to the ligament 30, e.g., at an angle from 0° to +/−15° from normal in the proximal or distal direction. Further, the curvilinear portion 10*a* includes a cut-adjacent curvilinear surface 16 configured to be positioned adjacent to the curvilinear cut 150. In embodiments, the cut-adjacent curvilinear surface 16 is positioned to be in alignment with the curvilinear cut 150. In embodiments, the cut-adjacent curvilinear surface 16 generally has the same shape, or substantially matches the shape, of the curvilinear cut 150. In some embodiments, the cut-adjacent curvilinear surface 16 has a plate radius 16*a*, which generally is similar to the radius 150*a* of the curvilinear cut 150 (see FIGS. 2A-2C and corresponding description). In embodiments, the curvilinear portion 10*a* has a curvilinear shape (see FIG. 1A), e.g., to generally match the shape of the curvilinear tibial cut 150. According to some embodiments, the curvilinear portion 10*a* of the epiphyseal tibial plate section 10 can comprise any of various shapes with a length 11*a* at least two times its width 13*a*, including having an elliptical, curved, curvilinear, or kidney bean-like shape.

Referring again to the implant device 100, as depicted in exemplary form in FIGS. 1A-1E, the epiphyseal tibial plate section 10 includes a proximal portion 10*b*. In embodiments, the proximal portion 10*b* is perpendicular to the curvilinear portion 10*a* and extends in the proximal direction relative to the curvilinear portion 10*a*. In some implementations, the proximal portion 10*b* is parallel to the ligament 30. In some embodiments, the proximal portion 10*b* is substantially parallel to the ligament 30, e.g., at an angle from 0° to +/−15° from parallel in the cranial or caudal direction. In embodiments, the proximal portion 10*b* has a width 13*b* that is substantially uniform. In embodiments, the width 13*b* is the same as the width 31 of the ligament 30. In other implementations, the width 13*b* differs from the width 31 of the ligament 30 by up to 10%, 15%, 20%, or even up to 25%. According to some embodiments, the proximal portion 10*b* of the epiphyseal tibial plate section 10 can comprise any of various shapes, including having a square, rectangular, elliptical, curved, curvilinear, or kidney bean-like shape.

Referring again to FIGS. 1A-1E, the TPLO implant device 100 further includes a metaphyseal tibial plate section 20 with at least three screw holes 22, an exterior surface 24*a*, and a bone-contacting surface 24*b*. Unless otherwise noted, each screw hole 22 of the metaphyseal tibial plate section 20 has a round shape and is configured to accept a bone screw 180 to secure the plate section 20 to a metaphyseal tibial bone fragment 120 (see also FIGS. 2A-2C and corresponding description below, showing the device 100 and screws 180, collectively implanted as implant assembly 200). The metaphyseal tibial plate section 20 is generally configured to secure a metaphyseal tibial bone fragment 120 defined from the TPLO procedure and, particularly, the curvilinear cut 150 to the tibial bone. Further, the metaphyseal tibial plate section 20 also serves to distribute stress uniformly across the curvilinear tibial cut 150.

Referring again to the implant device 100, as depicted in exemplary form in FIGS. 1A-1E, the metaphyseal tibial plate section 20 includes a cranial portion 20*a* and an elongated distal portion 20*b*. According to some embodiments, the cranial portion 20*a* is oriented in the cranial direction relative to the distal portion 20*b* and perpendicular to the ligament 30, as shown in FIGS. 1A-1E. In some implementations, the cranial portion 20*a* extends in the caudal direction relative to the position of the ligament 30, as also shown in FIGS. 1A-1E. In some embodiments, the cranial portion 20*a* is substantially perpendicular to the ligament 30, e.g., at an angle from 0° to +/−15° from normal in the proximal or distal direction toward, or away from, the curvilinear cut 150, respectively. According to some embodiments, the elongated distal portion 20*b* extends distally from the cranial portion 20*a*. In embodiments, the elongated distal portion 20*b* extends distally from the cranial portion 20*a* at an angle from 15° to 60°, 20° to 50°, 30° to 45°, or at any angle between the foregoing ranges, relative to the axis of the ligament 30 along its length 33.

Referring again to the implant device 100, as depicted in exemplary form in FIGS. 1A-1E, according to some embodiments, the cranial portion 20*a* of the metaphyseal tibial plate section 20 can comprise any of various shapes with a length 21*a* at least two times its width 23*a*, including having a square, rectangular, elliptical, curved, curvilinear, or kidney bean-like shape. According to some embodiments, the elongated distal portion 20*b* of the metaphyseal tibial plate section 20 can comprise any of various shapes with a length 21*b* at least 1.5×, 2×, 2.5×, 3×, 3.5×, or even 4× its width 23*b*, including having a square, rectangular, elliptical, curved, curvilinear, or kidney bean-like shape. In some implementations, the shapes of the cranial portion 20*a* of the metaphyseal tibial plate section 20 and the curvilinear portion 10*a* of the epiphyseal tibial plate section 10 generally match each other and/or the shape of the curvilinear tibial cut 150 (not shown in FIGS. 1A-1E). In other implementations, the shapes of the curvilinear portion 10*a* and the cranial portion 20*a* of the plate sections 10, 20, respectively, can differ from one another, e.g., as shown in FIGS. 1A-1E.

In some embodiments of the implant device 100, each of the epiphyseal and metaphyseal tibial plate sections 10, 20 can have an aspect ratio of at least 2:1 to ensure that the device 100 is slim and compact in size. As noted earlier, the relative slimness of the implant device 100 can facilitate relatively straightforward TPLO procedures with small incision sizes, short durations, lower implant reaction risk, and lower infection risk. In addition, the slim size of the implant device 100 employing tibial plate sections 10, 20 with high aspect ratios (at least 2:1) ensures that stresses can be uniformly distributed across the curvilinear cut 150, thus ensuring that the device 100 offers a stable securement of the epiphyseal bone fragment following the osteotomy.

Still referring to FIGS. 1A-1E, the TPLO implant device 100 further includes a ligament 30 configured to join the epiphyseal and metaphyseal tibial plate sections 10, 20. In embodiments, the ligament 30 is integral with the epiphyseal and metaphyseal tibial plate sections 10, 20 such that the implant device 100 can be fabricated from a single plate. In other embodiments (not shown), the ligament 30 is secured to both of the tibial plate sections 10, 20 by any appropriate method as understood by those skilled in the field of the disclosure appropriate for the material(s) (e.g., an implant grade metal alloy) of each of the plate sections 10, 20 and ligament 30 (e.g., welding, fastening, brazing, riveting, hot-pressing, etc.).

Referring again to FIGS. 1A-1E, the ligament 30 of the TPLO implant device 100 is configured to span the curvilinear tibial cut 150 (e.g., from a tibial plateau leveling osteotomy), in addition to joining the epiphyseal and metaphyseal tibial plate sections 10, 20. The ligament 30 can be defined by a ligament width 31 defined along an axis substantially parallel to an axis defined by each of the curvilinear and cranial portion lengths 11*a*, 21*a*, respectively. In some embodiments, the ligament width 31 is at least about 50%, 60%, 70%, 80%, 90%, or 95% shorter than each of the length dimensions of the implant device 100 (e.g., a ligament width 31 of ≤8 mm, which is at least about 50% shorter than portion lengths 11*a*, 11*b*, 21*a*, and 21*b*=16 mm), e.g., to ensure that the surgeon is able to observe the curvilinear cut 150 beside and/or through the ligament 30, and properly orient the TPLO implant device 100 during the TPLO procedure. The ligament 30 can also be defined by a ligament length 33, the length 33 dimension defined as being substantially normal to the ligament width 31. Further, as depicted in exemplary form in FIGS. 1A-1E, the ligament 30 can comprise a single connection between the tibial plate sections 10, 20. In some implementations (not shown), the ligament 30 can comprise multiple bands, joints, ligaments, or other elements situated between the tibial plate sections 10, 20 to join them and facilitate visibility to the curvilinear cut 150 beneath the TPLO implant device 100. In such implementations, the multiple bands, joints, ligaments, or other elements collectively define the ligament width 31 and length 33.

Referring again to FIGS. 1A-1E, each of the metaphyseal and epiphyseal tibial plate sections 10, 20 (including the curvilinear portion 10*a*, proximal portion 10*b*, cranial portion 20*a* and elongated distal portion 20*b*) and the ligament 30 can be fabricated from an implant grade alloy, as understood by those skilled in the field of the disclosure. Suitable implant grade alloys include stainless steel alloys (e.g., SS 316, SS 316LVM, SS 304, and 17-4 PH) titanium alloys (e.g., Ti-6Al-4V, Ti-6Al-7Nb, Grade 2, and Grade 4). Each of the tibial plate sections 10, 20 and ligament 30 can be fabricated from the same implant grade alloy. In addition, each of the bone screws 180 employed in connection with a TPLO procedure to install an implant device 100 of the disclosure can be fabricated from the same implant grade alloy as used for the plate sections 10, 20 and the ligament 30. Further, various surface finishes and roughness levels of the epiphyseal tibial plate section 10, metaphyseal tibial plate section 20 and ligament 30 are acceptable, as deemed by those skilled in the field of the disclosure to be suitable for the application and manufacturing of the TPLO implant device 100. In an embodiment of the implant device 100, each of the epiphyseal tibial plate section 10, metaphyseal tibial plate section 20 and ligament 30 are manufactured such that their surfaces (e.g., exterior surfaces 14*a*, 24*a* and bone-contacting surfaces 14*b*, 24*b*) can have a matte finish (e.g., with a surface roughness from 20 to 60 μm (Ra)).

Figure 1B:
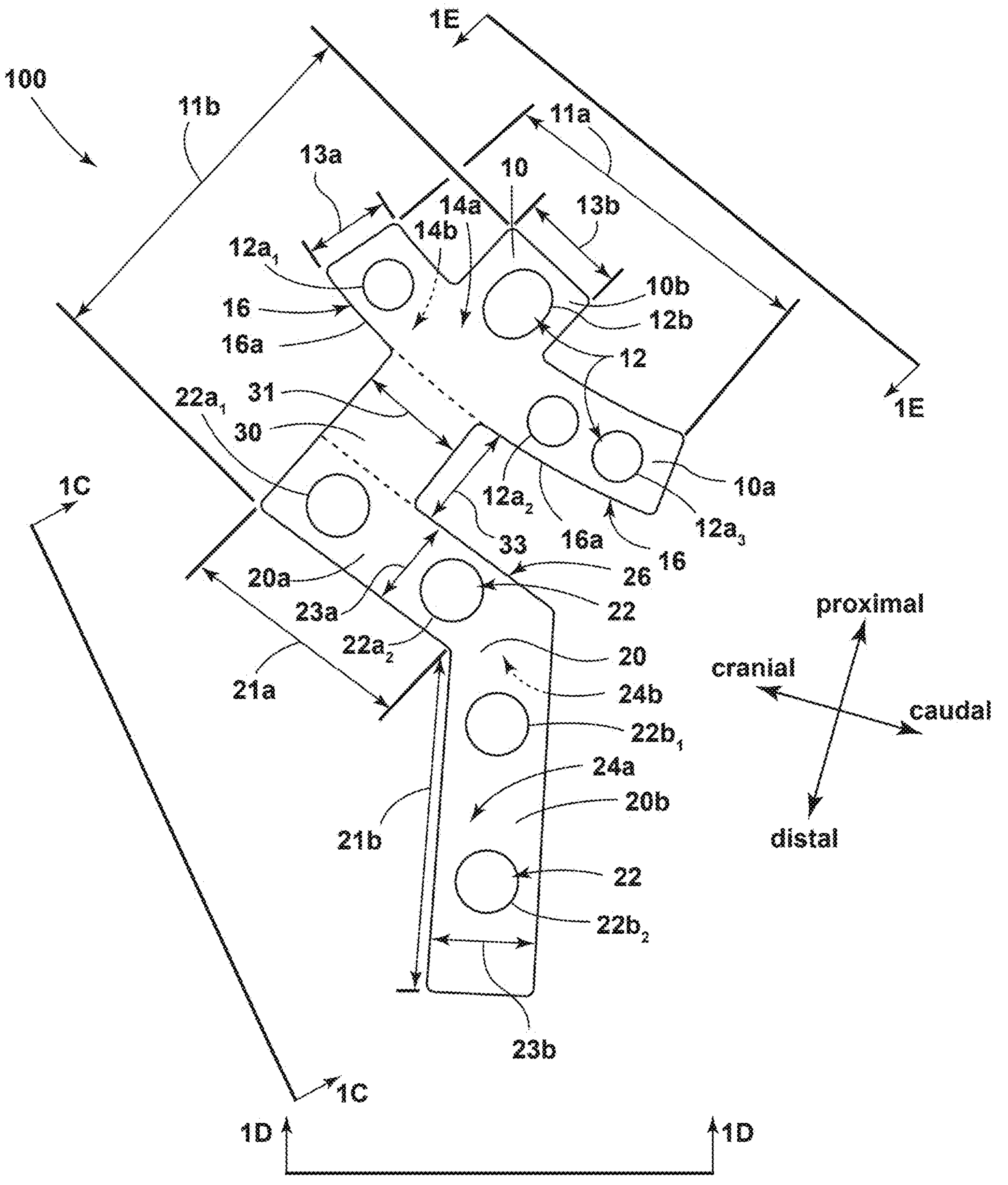
FIG. 1B is a top plan view of the implant device of FIG. 1A.

Still referring to the TPLO implant device 100 of FIGS. 1A-1E, the curvilinear portion 10*a* of the epiphyseal tibial plate section 10 can be defined by a curvilinear portion length 11*a* and width 13*a*. Further, the proximal portion 10*b* can be a defined by a proximal portion width 13*b*. In addition, the cranial portion 20*a* of the metaphyseal tibial plate section 20 can be defined by a cranial portion length 21*a* and width 23*a*, and the elongated distal portion 20*b* can be defined by an elongated distal portion length 21*b* and width 23*b*. The implant device 100 can also be characterized by a length 11*b*, which as shown in FIGS. 1A-1B, is defined by the sum of the width 13*a* of the curvilinear portion 10*a*, length of the proximal portion 10*b*, length 33 of the ligament 30 and width 23*a* of the cranial portion 20*a*. Further, according to some implementations of the implant device 100, each of the widths 13*a*, 13*b*, 23*a*, 23*b*, and 31 of the tibial plate sections 10, 20 and ligament 30, respectively, is substantially uniform. In some embodiments, the width 13*a*, 13*b*, 23*a*, 23*b*, and 31 of each of the tibial plate sections 10, 20 and ligament 30, respectively, is both uniform and varies by no more than +10%, 5%, 1%, 0.1%, 0.01%, or even less, as only limited by machining capability and the materials selected for the tibial plate sections 10, 20 and ligament 30. Further, according to some embodiments of the implant device 100, each length 11*a*, 11*b*, 21*a*, and 21*b* of the tibial plate sections 10, 20, respectively, is at least two times, three times, or four times longer than the respective widths 13*a*, 13*b*, 23*a*, 23*b*, and 31 of the tibial plate sections 10, 20 and ligament 30, respectively. According to some implementations, each of the width 31 of the ligament 30 and width 13*b* of the proximal portion 10*b* is greater than the width 13*a* of the curvilinear portion 10*a*, width 23*b* of the elongated distal portion 20*b*, and width 23*a* of the cranial portion 20*a*, as shown in exemplary form in FIGS. 1A-1E.

According to embodiments of the TPLO implant device 100 shown in exemplary form in FIGS. 1A-1E, the aspect ratio of each of the tibial plate sections 10, 20 and ligament 30 (i.e., ratio of lengths 11*a*, 11*b*, 21*a*, and 21*b* to widths 13*a*, 13*b*, 23*a*, and 23*b*, respectively) is at least 2:1, 2.5:1, 3:1, 3.5:1, 4:1, 5:1, and all aspect ratios between and greater than the foregoing aspect ratios. With regard to these embodiments, an implant device 100 with tibial plate sections 10, 20 having high aspect ratios of at least 2:1 ensures that the device is relatively slim in size. Further, as noted earlier, the slim size of the implant device 100 can facilitate straightforward TPLO procedures with small incision sizes, short durations, low implant reaction risk, and low infection risk. In addition, the relatively small size of the implant device 100 employing tibial plate sections 10, 20 and ligament 30 with high aspect ratios (at least 2:1) also ensures that stresses can be uniformly distributed across the curvilinear cut 150, thus ensuring that the device 100 offers a stable securement of the proximal portion of the tibia following a TPLO procedure.

Referring again to the TPLO implant device 100 depicted in FIGS. 1A-1E, according to some embodiments, the epiphyseal tibial plate section 10 can be configured with a curvilinear portion 10*a* such that its length 11*a* is from 6 mm to 24 mm or 8 mm to 20 mm, and its width 13*a* is from 2 mm to 12 mm or 3 mm to 10 mm. In some implementations, the curvilinear portion length 11*a* can be 6 mm, 8 mm, 10 mm, 12 mm, 14 mm, 16 mm, 18 mm, 20 mm, 22 mm, 24 mm, or any length 11*a* between any of the foregoing length values. In some implementations, the width 13*a* of the curvilinear portion 10*a* can be 2 mm, 3 mm, 4 mm, 5 mm, 6 mm, 7 mm, 8 mm, 9 mm, 10 mm, 11 mm, 12 mm, or any width 13*a* between any of the foregoing width values. For example, according to some embodiments, the length 11*a* of the curvilinear portion 10*a* can be 2 times, 2.5 times, 3 times, 3.5 times, 4 times, 4.5 times, 5 times, or any factor between the foregoing, of its width 13*a*. Unless otherwise noted, the length 11*a* is defined as the longest dimension of the curvilinear portion 10*a* and the width 13*a* is defined as the shorter dimension of the curvilinear portion 10*a* running along its length 11*a*.

Referring again to the TPLO implant device 100 depicted in FIGS. 1A-1E, according to some embodiments, the epiphyseal tibial plate section 10 can be configured with a proximal portion 10*b* such that its length 11*b* (as defined as being inclusive of the width 13*a*, length 33 and width 23*a*, as shown in FIG. 1A) is from 10 mm to 36 mm or 13 mm to 34 mm, and its width 13*b* is from 3 mm to 17 mm or 5 mm to 15 mm. In some implementations, the proximal portion length 11*b* can be 10 mm, 12 mm, 13 mm, 14 mm, 16 mm, 18 mm, 20 mm, 22 mm, 24 mm, 26 mm, 28 mm, 30 mm, 32 mm, 34 mm, 36 mm, or any length 11*b* between any of the foregoing length values. In some implementations, the width 13*b* of the proximal portion 10*b* can be 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, or any width 13*b* between any of the foregoing width values. For example, according to some embodiments, the length 11*b* of the proximal portion 10*b* can be 2 times, 2.5 times, 3 times, 3.5 times, 4 times, 4.5 times, 5 times, or any factor between the foregoing, of its width 13*b*. Unless otherwise noted, the length 11*b* is defined as the longest dimension of epiphyseal tibial plate section 10 and the proximal portion 10*b* (note that the width 13*b* is defined as the shortest dimension of the proximal portion 10*b*), i.e., the sum of the width 13*a* of the curvilinear portion 10*a*, length 33 of the ligament 30, and width 23*a* of the cranial portion 20*a*.

Still referring to the TPLO implant device 100 depicted in FIGS. 1A-1E, according to some embodiments, the metaphyseal tibial plate section 20 can be configured with a cranial portion 20*a* such that its length 21*a* is from 2 mm to 13 mm or 4 mm to 11.5 mm, and its width 23*a* is from 3 mm to 15 mm or 4.5 mm to 12 mm. In some implementations, the cranial portion length 21*a* can be 2 mm, 3 mm, 4 mm, 5 mm, 6 mm, 7 mm, 8 mm, 9 mm, 10 mm, 11 mm, 11.5 mm, 12 mm, 13 mm, or any length 21*a* between any of the foregoing length values. In some implementations, the width 23*a* of the cranial portion 20*a* can be 3 mm, 4 mm, 4.5 mm, 5 mm, 6 mm, 7 mm, 8 mm, 9 mm, 10 mm, 11 mm, 12 mm, 13 mm, 14 mm, 15 mm, or any width 23*a* between the foregoing width values. For example, according to some embodiments, the length 21*a* of the cranial portion 20*a* can be 2 times, 2.5 times, 3 times, 3.5 times, 4 times, 4.5 times, 5 times, or any factor between the foregoing, of width 23*a*. Further, unless otherwise noted, the length 21*a* of the cranial portion 20*a* is defined as the longest dimension of the cranial portion 20*a* and the width 23*a* is defined as the shorter dimension of the cranial portion 20*a* along its length 21*a*.

Still referring to the TPLO implant device 100 depicted in FIGS. 1A-1E, according to some embodiments, the metaphyseal tibial plate section 20 can be configured with an elongated distal portion 20*b* such that its length 21*b* is from 10 mm to 35 mm or 12 mm to 32 mm, and its width 23*b* is from 3 mm to 15 mm or 4.5 mm to 12 mm. In some implementations, the elongated distal portion length 21*b* can be 10 mm, 11 mm, 12 mm, 13 mm, 14 mm, 16 mm, 18 mm, 20 mm, 22 mm, 24 mm, 26 mm, 28 mm, 30 mm, 32 mm, 33 mm, 34 mm, 35 mm, or any length 21*b* between any of the foregoing length values. In some implementations, the width 23*b* of the elongated distal portion 20*b* can be 3 mm, 4 mm, 4.5 mm, 5 mm, 6 mm, 7 mm, 8 mm, 9 mm, 10 mm, 11 mm, 12 mm, 13 mm, 14 mm, 15 mm, or any width 23*b* between any of the foregoing width values. For example, according to some embodiments, the length 21*b* of the elongated distal portion 20*b* can be 2 times, 2.5 times, 3 times, 3.5 times, 4 times, 4.5 times, 5 times, or any factor between the foregoing, of width 23*b*. Further, unless otherwise noted, the length 21*b* of the elongated distal portion 20*b* is defined as the longest dimension of the elongated distal portion 20*b* and the width 23*b* is defined as the shorter dimension of the elongated distal portion 20*b* along its length 21*b*.

Referring again to the TPLO implant device 100 depicted in FIGS. 1A-1E, according to some embodiments, the ligament 30 can be configured such that its width 31 is from 4 mm to 16 mm, 4 mm to 15 mm, 5 mm to 15 mm, and all ligament widths 31 between the foregoing width ranges. Further, the ligament 30 can be configured such that its length 33 is from 4 mm to 15 mm, 4 mm to 12.5 mm, 4 mm to 10 mm, and all ligament lengths 31 between the foregoing width ranges. As noted earlier, in some embodiments of the implant device 100, the ligament width 31 can be at least about 50% shorter than each of the portion lengths 11*a*, 11*b*, 21*a*, and 21*b*. For example, the ligament width 31 can be at least 50%, 55%, 60%, 70%, 80%, 90%, 95%, or even 100% shorter than each of the portion lengths 11*a*, 11*b*, 21*a*, and 21*b*. These dimensional configurations of the ligament 30 can ensure that the surgeon is able to observe the curvilinear cut 150 beside and/or through the ligament 30, and properly orient the implant device 100 during implantation in the TPLO procedure (see FIGS. 2A-2C and corresponding description below).

According to embodiments of the TPLO implant device 100 depicted in FIGS. 1A-1E, each of the epiphyseal tibial plate section 10, metaphyseal tibial plate section 20 and ligament 30 can be further defined by respective thicknesses 18, 28, and 38. In some embodiments, the thickness 18 of the epiphyseal tibial plate section 10 can range from 1 mm to 5 mm. For example, the thickness 18 can be 1 mm to 4 mm, 1.25 mm to 5 mm, 1.25 mm to 4 mm, 1.5 mm to 5 mm, 1.5 mm to 4 mm, and all thicknesses 18 between the foregoing thickness values. In some embodiments, the thickness 28 of the metaphyseal tibial plate section 20 can range from 1 mm to 5 mm. For example, the thickness 28 can be 1 mm to 4 mm, 1.25 mm to 5 mm, 1.25 mm to 4 mm, 1.5 mm to 5 mm, 1.5 mm to 4 mm, and all thicknesses 28 between the foregoing thickness values. Further, according to some embodiments, the thickness 38 of the ligament 30 can range from 1 mm to 5 mm. For example, the thickness 38 can be 1 mm to 4 mm, 1.25 mm to 5 mm, 1.25 mm to 4 mm, 1.5 mm to 5 mm, 1.5 mm to 4 mm, and all thicknesses 38 between the foregoing thickness values. In some implementations of the implant device 100, the thicknesses 18, 28, and 38 of the plate sections 10, 20 and ligament 30, respectively, can differ from one another. In some embodiments, the thickness 18 of the epiphyseal tibial plate section 10 can be smaller than the respective thicknesses 28 and 38 of the metaphyseal tibial plate section 20 and ligament 30, respectively, e.g., from 1.5 mm to 4 mm vs. 2 mm to 4 mm.

Referring again to the TPLO implant device 100 depicted in FIGS. 1A-1E, each of the epiphyseal and metaphyseal tibial plate sections 10, 20 can include at least three (3) screw holes 12, 22, respectively. In some embodiments, each of the epiphyseal and metaphyseal tibial plate sections 10, 20 can include from three (3) to twelve (12), three (3) to ten (10), or three (3) to eight (8) screw holes 12, 22, respectively, along with any number of screw holes 12, 22 between the foregoing ranges. For example, each of the epiphyseal and metaphyseal tibial plate sections 10, 20 can include 3, 4, 5, 6, 7, 8, 9, 10, 11, or even 12 screw holes 12, 22, respectively. Further, according to some implementations of the implant device 100, one of the screw holes 12 of the epiphyseal tibial plate section 10 can be a single elongated screw hole 12*b* (e.g., the proximal-most screw hole) that is elongated in a direction perpendicular to a curvilinear cut 150 of the tibial bone to receive a round screw 180, as shown in exemplary form in FIGS. 1A-1E.

According to embodiments, each of the screw holes 12, 22 comprises a round shape suitable to receive a screw 180, which also comprises a round shaped head. In some embodiments, each of the epiphyseal and metaphyseal tibial plate sections 10, 20 has the same number of screw holes 12 (and 12*b*, if applicable), 22, respectively. In other embodiments, particularly those in which the metaphyseal tibial plate section length (i.e., the sum of the cranial and elongated distal portion lengths 21*a* and 21*b*) is longer than the curvilinear portion length 11*a*, the number of screw holes 22 in the metaphyseal tibial plate section 20 is greater than the number of screw holes 12 in the epiphyseal tibial plate section 10. In general, the spacing and arrangement of the screw holes 12 (and 12*b*, if applicable), 22, respectively, in the plate sections 10, 20 can be equal or differ, as determined by the shape of the plate sections 10, 20 and engineering and plate machining considerations understood by those skilled in the field of the disclosure. In embodiments, each of the screw holes 12, (and 12*b*, if applicable), 22 are distributed within the plate sections 10, 20 and no holes 12, 12*b* or 22 are present in the ligament 30, as shown in exemplary form in the implant device 100 of FIGS. 1A-1E.

Figure 1C:
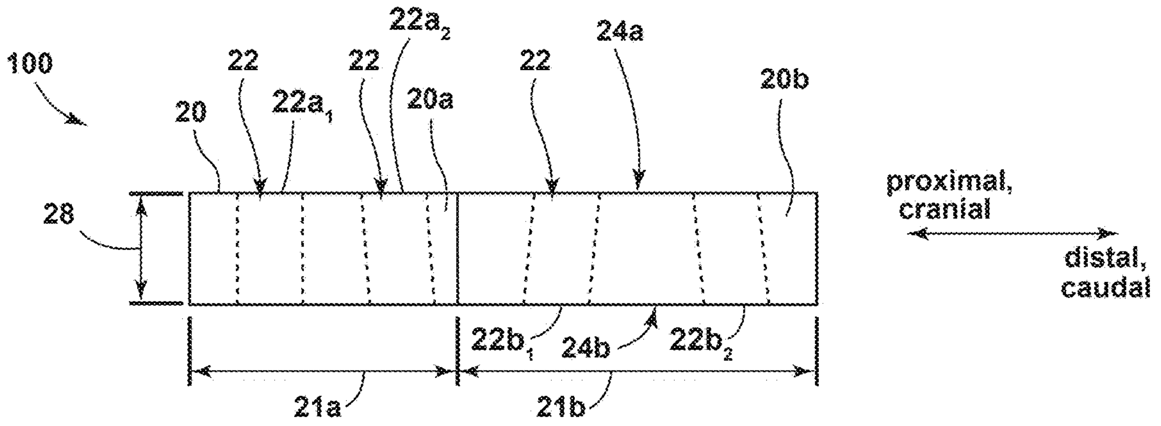
FIG. 1C is an end-on view of the implant device of FIG. 1A from line 1C-1C in FIG. 1B.

Referring again to the implant device 100 of FIGS. 1A-1E, various configurations of the screw holes 12 can be positioned in the epiphyseal tibial plate section 10. According to an exemplary embodiment, as depicted in FIGS. 1A-1E, the proximal portion 10*b* has one screw hole 12*b* with an oblong shape and the curvilinear portion 10*a* has at least three screw holes 12. For example, as shown in FIGS. 1A-1C, the curvilinear portion 10*a* can have one screw hole 12*$a_1$* positioned cranially relative to the ligament 30 and proximal portion 10*b*, a second screw hole 12*$a_2$* positioned caudally relative to the ligament 30 and the proximal portion 10*b*, and a third screw hole 12*$a_3$* positioned caudally relative to the second screw hole 12*$a_2$*.

Still referring to the implant device 100 of FIGS. 1A-1E, various configurations of the screw holes 22 can be positioned in the metaphyseal tibial plate section 20. According to an embodiment, as depicted in FIGS. 1A-1E, the cranial portion 20*a* can have two screw holes 22 and the elongated distal portion 20*b* can have at least two screw holes 22. In an embodiment, the cranial portion 20*a* can have a first screw hole 22*$a_1$* positioned distally from the ligament 30 and a second screw hole 22*$a_2$* positioned caudally from the first screw hole 22*$a_1$*. In an embodiment, the elongated distal portion 20*b* can have a first screw hole 22*$b_1$* positioned distally from the cranial portion 20*a* and a second screw hole 22*$b_2$* positioned distally from the first screw hole 22*$b_1$*.

Still referring to FIGS. 1A-1E, the TPLO implant device 100 can be configured such that each of the epiphyseal and metaphyseal tibial plate sections 10, 20 comprises a cut-adjacent curvilinear surface 16 and a cut-adjacent surface 26, each of which is substantially normal to its bone-contacting surface 14*b*, 24*b* (and normal to its exterior surface 14*a*, 24*a*), respectively. Further, the cut-adjacent curvilinear surface 16 can comprise a plate radius 16*a* within +25% of the curvilinear cut radius 150*a* of the curvilinear cut 150 (see FIGS. 2A-2C, described in further detail below). In embodiments, the plate radius 16*a* of the cut-adjacent curvilinear surface 16 of the epiphyseal tibial plate section 10, particularly its curvilinear portion 10*a*, is within +25%, 20%, 15%, 10%, 5%, or even 1% of the curvilinear cut radius 150*a*. In embodiments, the plate radius 16*a* of the cut-adjacent curvilinear surface 16 can range from 10 mm to 30 mm, e.g., 10 mm, 12 mm, 14 mm, 16 mm, 18 mm, 20 mm, 22 mm, 24 mm, 26 mm, 28 mm, 30 mm, or any radius value between the foregoing. In general, the foregoing configurations relate to shapes of the epiphyseal tibial plate section 10, particularly the curvilinear portion 10*a*, with a cut-adjacent curvilinear surface 16 that generally matches the shape of the curvilinear cut 150, including its radius 150*a*, to ensure a uniform distribution of stress and an optimal reinforcement between the epiphyseal and metaphyseal tibial fragments 110, 120.

Referring again to the TPLO implant device 100 depicted in exemplary form in FIGS. 1A-1E, it should be understood that the curvilinear cut 150 of the tibia bone (i.e., as secured by the device 100) is defined by a curvilinear cut radius 150*a* and separates the epiphyseal and metaphyseal tibial bone fragments 110, 120 (see FIGS. 2A-2C, described in further detail below). In general, the practitioner of a TPLO procedure can use an appropriate power tool, as understood by those skilled in the field of the disclosure (e.g., a deSoutter MBQ-708 Vdrive drill, as procured from Movora (a veterinary component supplier)), to make a curvilinear cut to the tibia to form a cut radius 150*a* that ranges from 5 mm to 35 mm. More particularly, the TPLO practitioner uses a saw blade with a sawblade number that corresponds to the desired cut radius 150*a* (e.g., TPLO Saw Blade Nos. 8-30, as procured from Movora (a veterinary component supplier), that correspond to cut radii 8-30 mm, respectively) to form the cut 150. For example, the curvilinear cut radius 150*a* of the curvilinear cut 150 can be 8 mm, 10 mm, 12 mm, 15 mm, 18 mm, 20 mm, 24 mm, 27 mm, 30 mm, or any cut radius value between the foregoing radii.

Figure 1D:
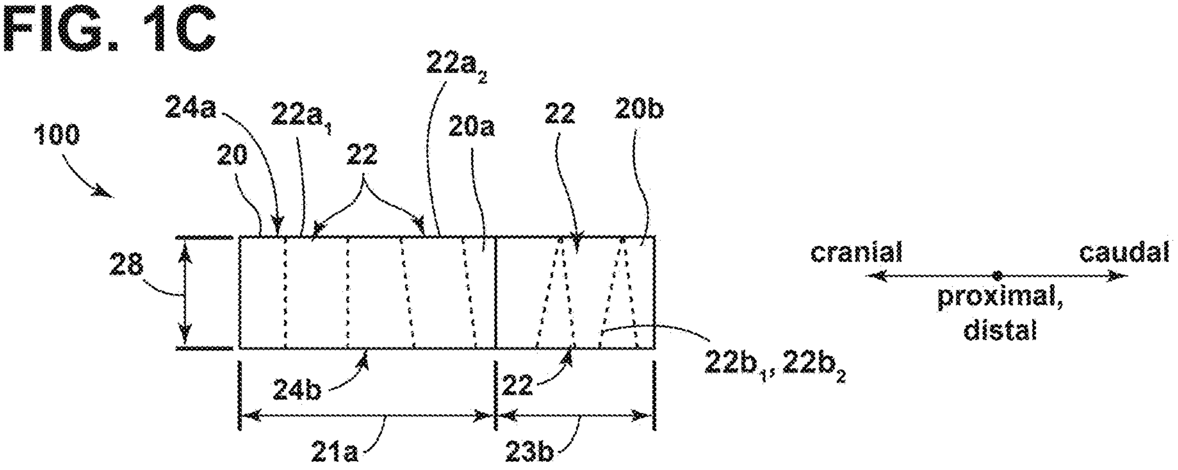
FIG. 1D is an end-on view of the implant device of FIG. 1A from line 1D-1D in FIG. 1B.

Referring now to FIGS. 1C and 1D, end-on views of the metaphyseal tibial plate section 20, including cranial portion 20*a* and elongated distal portion 20*b*, of the implant device 100 of FIGS. 1A-1B are provided, as viewed from lines 1C-1C and 1D-1D (see FIG. 1B), respectively, showing the screw holes 22 and thickness 28. The screw holes 22 run through the plate section 20 from the exterior surface 24*a* to the bone-contacting surface 24*b*. Further, according to an embodiment, the first screw hole 22*$a_1$* of the cranial portion 20*a* is oriented substantially normal to the exterior and bone-contacting surfaces 24*a* and 24*b*, respectively; and the second screw hole 22*$a_2$* of the cranial portion 20*a* is oriented caudally from 5° to 15° or 7° to 13° from normal to the exterior and bone-contacting surfaces 24*a* and 24*b*, respectively. According to another embodiment, the first screw hole 22*$b_1$* of the elongated distal portion 20*b* is oriented cranially from 5° to 15° or 7° to 13° from normal to the exterior and bone-contacting surfaces 24*a* and 24*b*, respectively; and the second screw hole 22*$b_2$* of the elongated distal portion 20*b* is oriented caudally from 5° to 15° or 7° to 13° from normal to the exterior and bone-contacting surfaces 24*a* and 24*b*, respectively.

Figure 1E:
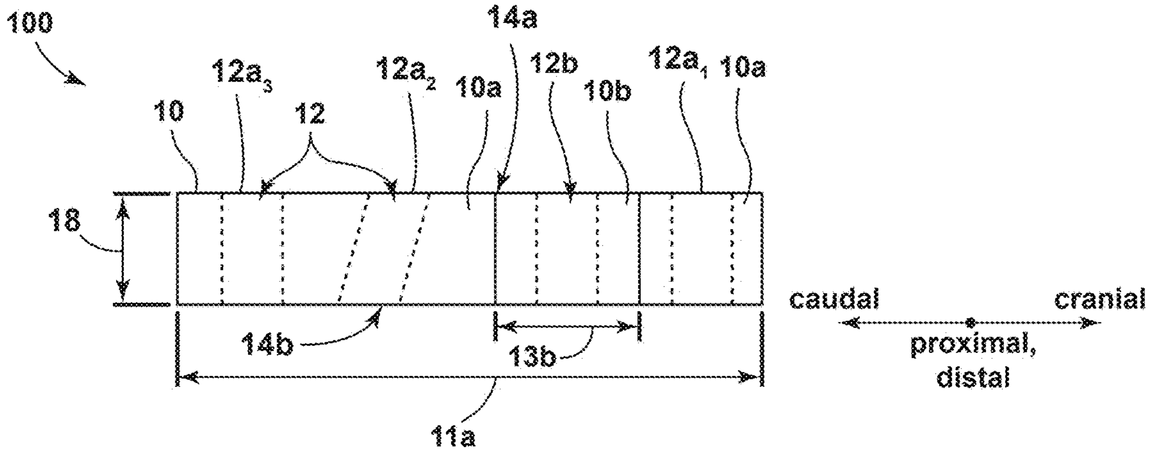
FIG. 1E is an end-on view of the implant device of FIG. 1A from line 1E-1E in FIG. 1B.

Referring now to FIG. 1E, an end-on view of the epiphyseal tibial plate section 10, including curvilinear portion 10*a* and proximal portion 10*b*, of the implant device 100 of FIGS. 1A-1B is provided, as viewed from line 1E-1E (see FIG. 1B) showing the screw holes 12 and thickness 18. The screw holes 12 run through the plate section 10 from the exterior surface 14*a* to the bone-contacting surface 14*b*. Further, according to an embodiment, the first and third screw holes 12*$a_1$* and 12*$a_3$* of the curvilinear portion 10*a*, respectively, are oriented substantially normal to the exterior and bone-contacting surfaces 14*a* and 14*b*, respectively; and the second screw hole 12*$a_2$* of the curvilinear portion 10*a* is oriented both proximally and caudally from 5° to 15° or 7° to 13° from normal to the exterior and bone-contacting surfaces 14*a* and 14*b*, respectively. According to another embodiment, the first screw hole 12*b* of the proximal portion 10*b* is oriented substantially normal to the exterior and bone-contacting surfaces 14*a* and 14*b*, respectively.

According to implementations of the implant device 100, the holes 12, 22 of the epiphyseal and metaphyseal tibial plate sections 10, 20, respectively, are round. Further, the holes 12, 22 of the plate sections 10, 20, respectively, can have countersink, beveled edges in proximity to the exterior surfaces 14*a*, 24*a*. According to some embodiments of the implant device 100, each of the holes 12, 12*b*, and 22 can be configured to accommodate screws 180, which are locking or non-locking in their configuration. Further, according to implementations of the implant device 100, the screw holes 12, 12*b*, and 22 can have a diameter that ranges from 1.5 mm to 3.5 mm (or the longest width dimension for elongated holes 12*b*), including any diameter value between the foregoing, and be capable of securing screws 180 with various diameters within this range. Further, according to some implementations of the implant device 100, one of, some of, or all of the screw holes 12, 12*b*, and 22 of the epiphyseal and metaphyseal tibial plate sections 10, 20 can be oriented in the cranial or caudal directions and/or the proximal or distal directions from 5° to 15° from normal to the exterior and bone-contacting surfaces 14*a*, 14*b*, 24*a*, and 24*b*, respectively. As one skilled in the field of the disclosure will appreciate, these orientation(s) of the screw holes 12, 12*b*, and 22 away from normal can be selected to ensure that the screws 180 are positioned to maximize the amount of bone mass secured in view of the particular location of the hole(s), 12, 12*b*, and 22 in the implant device 100, the size of the implant device 100, and the size of the tibial bone of the animal with the device 100 as implanted.

Figure 2A:
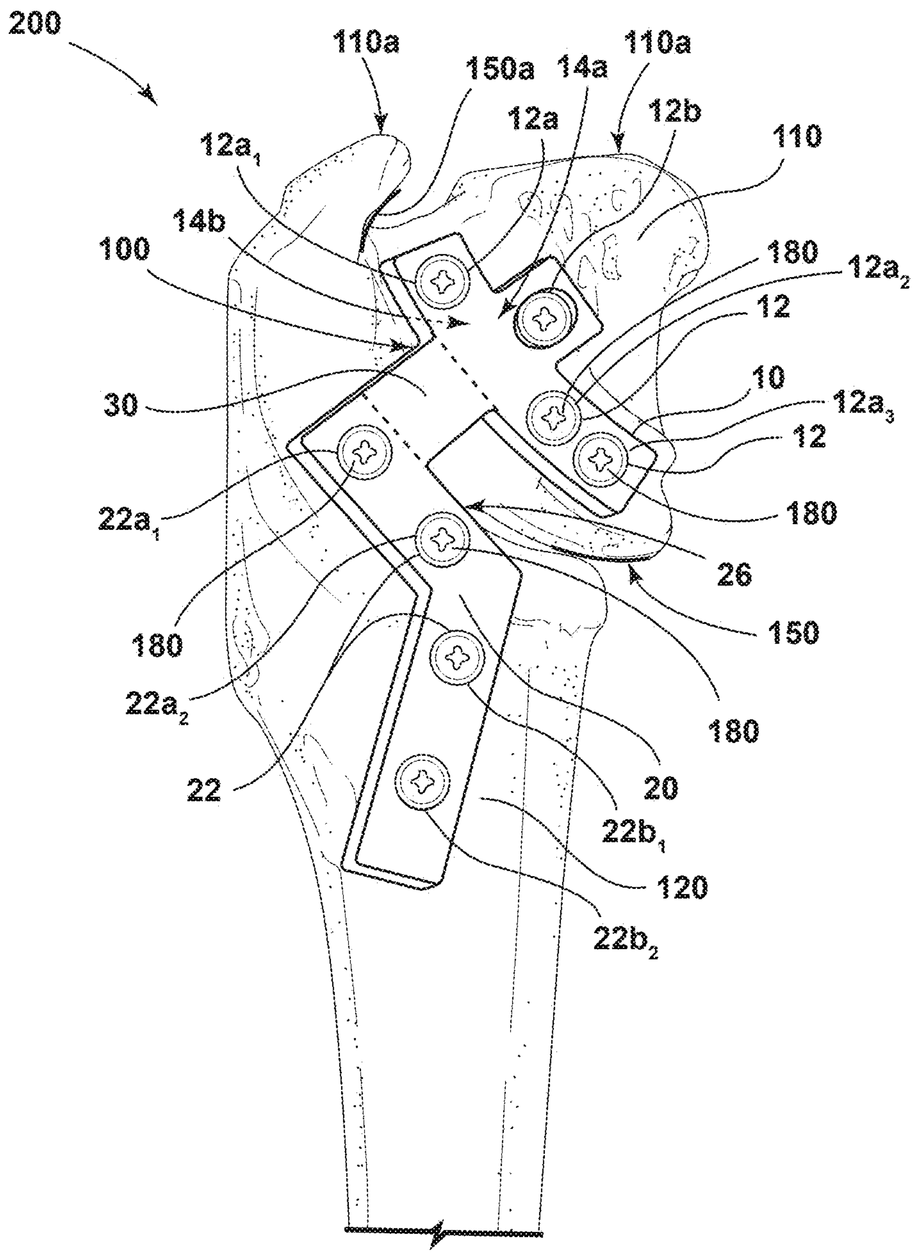
FIG. 2A is a perspective front view of an implant assembly comprising the implant device of FIG. 1A, as secured to epiphyseal and metaphyseal tibial bone fragments across a curvilinear tibial cut, according to an embodiment of the disclosure.
Figure 2B:
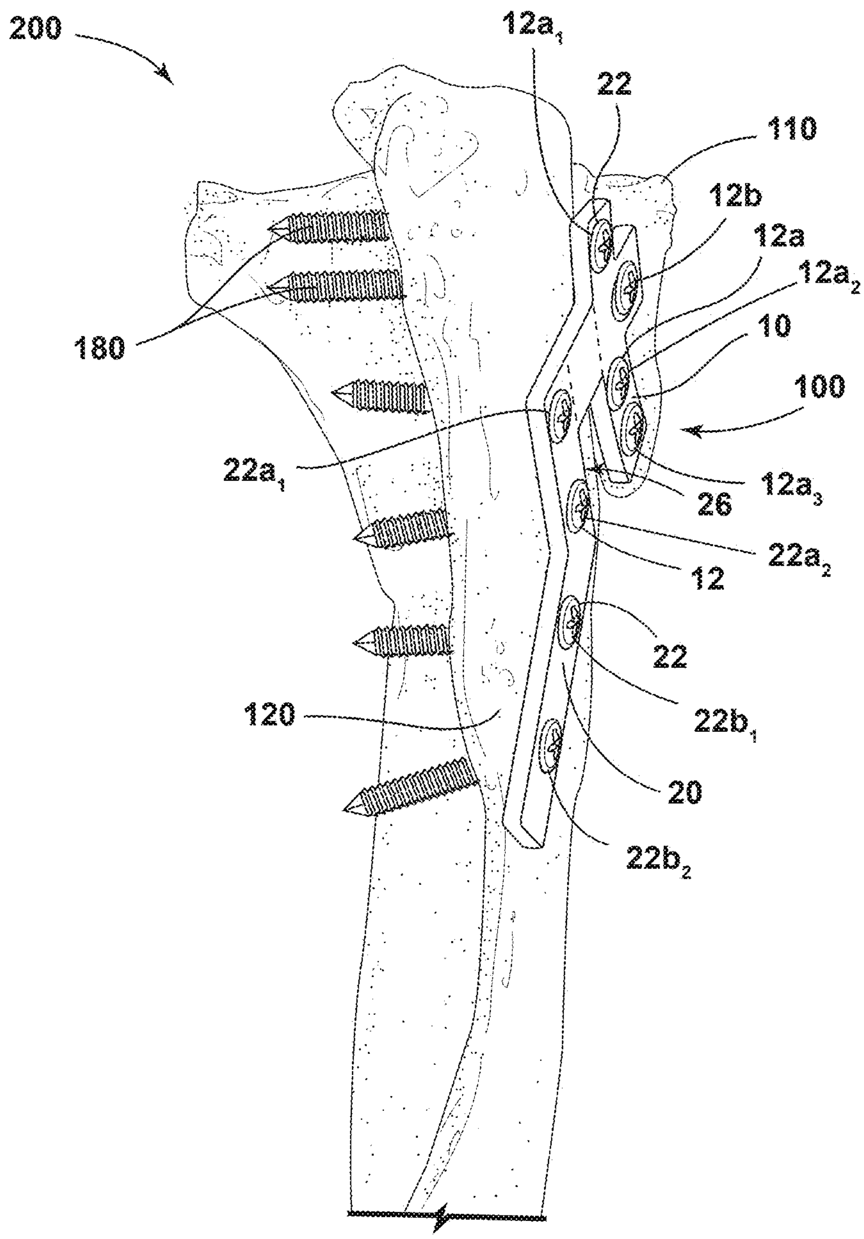
FIG. 2B is a 90° counterclockwise-rotated perspective view of the implant assembly of FIG. 2A.
Figure 2C:
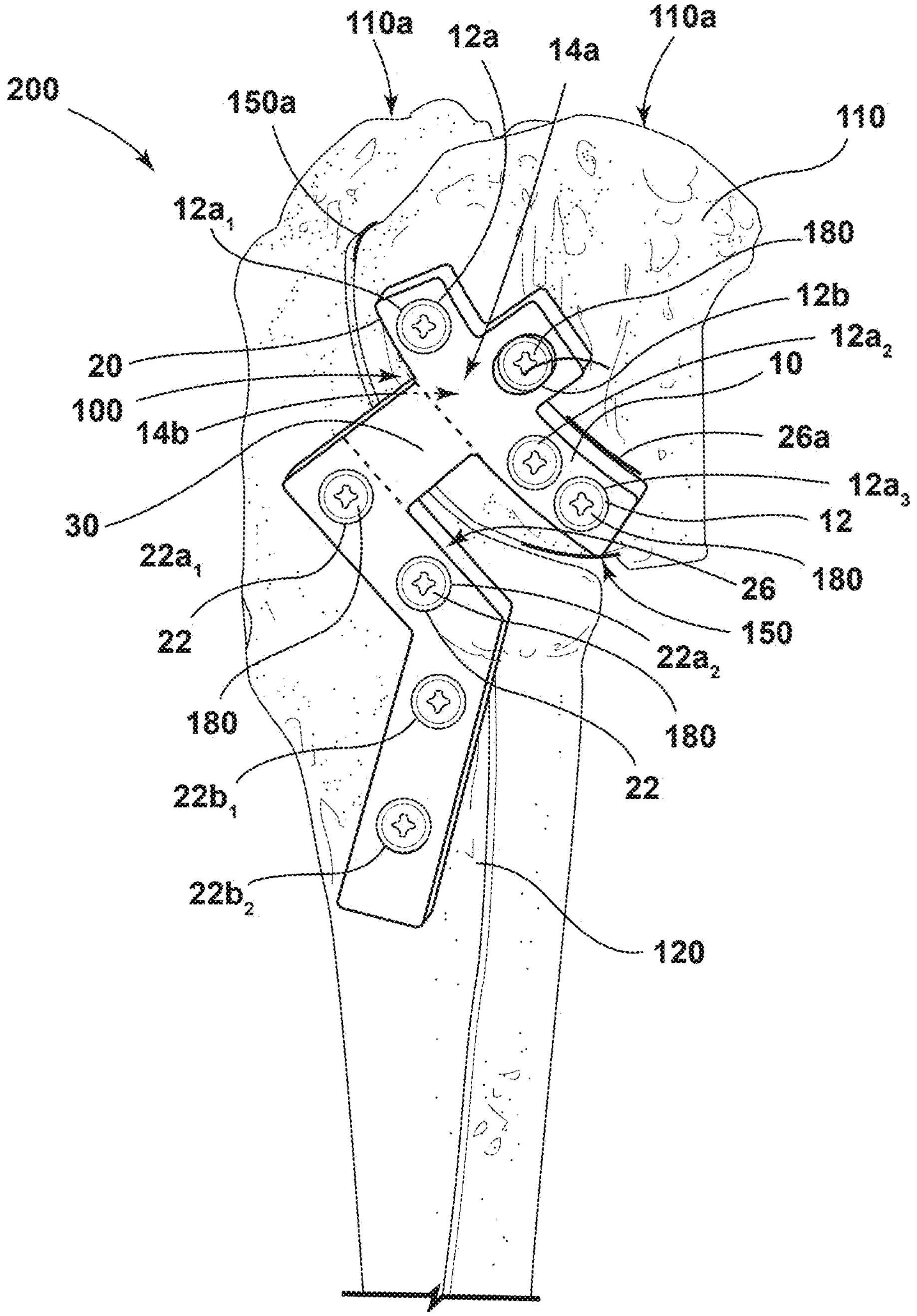
FIG. 2C is a ~10° clockwise-rotated perspective view of the implant assembly of FIG. 2A.

Referring now to FIGS. 2A-2C, an implant assembly 200 is shown in various perspective views, e.g., as secured to the left tibia of the foreleg of an animal. The implant assembly 200 includes a TPLO implant device 100 configured according to principles of the disclosure (see FIGS. 1A-1E and corresponding description above), as secured to epiphyseal and metaphyseal tibial bone fragments 110, 120 across a curvilinear tibial cut 150. It should be understood that the implant device 100 can be configured for attachment to a right tibia by adjusting the arrangement of the various portions and sections of the device according to the principles of this disclosure, as would be understood by those skilled in the field of the disclosure. As is evident from these figures, the implant device 100 is installed by a practitioner during a TPLO procedure. Notably, the practitioner installs the implant device 100 after the curvilinear cut 150 is made to separate the epiphyseal and metaphyseal tibial bone fragments 110, 120 (e.g., as using Saw Blade Nos. 8-30 from Movora), and the epiphyseal tibial bone fragment 110 has been rotated in a clockwise direction for the left leg and in a counterclockwise direction for the right leg along the curvilinear cut 150 to level the tibial bone plateau 110*a*. Once the tibial bone plateau 110*a* has been leveled by the practitioner, the implant device 100 is affixed to the epiphyseal and metaphyseal tibial bone fragments 110, 120 by bone screws 180, as inserted through holes 12, 22, and any elongated hole 12*b*, if present. For embodiments of the implant device 100 (see FIGS. 2A-2C) that comprise an elongated hole 12*b* in the epiphyseal tibial plate section 10, the screw 180 used in this hole is adjusted by the practitioner within the hole relative to the curvilinear cut 150 to increase the compressive forces between the tibial bone fragments 110, 120. As is also evident from the figures, the implant device 100 is installed such that the ligament 30 spans the curvilinear cut 150; and the cut-adjacent curvilinear surface 16 of the epiphyseal tibial plate section 10, particularly its curvilinear portion 10*a*, is aligned along the curvilinear cut 150.

Referring now to Table 1 below, dimensions are provided of the epiphyseal and metaphyseal tibial plate sections 10, 20 and ligament 30 of various implant devices 100 (see, e.g., FIGS. 1A-1E and corresponding description above). As is detailed below in Table 1, various dimensions (in mm) are provided for exemplary implant devices A10, B12, C15, D18, E21, F24, G27, and H30, each successively larger and intended for successively larger host animals. In particular, Table 1 provides the following dimensions for these exemplary implant devices 100: curvilinear portion length 11*a* and width 13*a*; the proximal portion length 11*b* (i.e., as inclusive of the length of the proximal portion 10*b*, width 23*a*, length 33 and width 13*a*) and width 13*b*; cranial portion length 21*a* and width 23*a*; and elongated distal portion length 21*b* and width 23*b*.

TABLE 1

Illustrative TPLO implant device configurations

| Implant device | Widths (mm) | | | | Thickness (mm) | | Lengths (mm) | | | |
|---|---|---|---|---|---|---|---|---|---|---|
| (see FIGS. 1A-1E) | 13a | 13b | 23a | 23b | 18 | 28, 38 | 11a | 11b | 21a | 21b |
| A10 | 3 | 5 | 4.5 | 4.5 | 1.5 | 2 | 8 | 13 | 4 | 12 |
| B12 | 4 | 6 | 5 | 5 | 1.5 | 2 | 10 | 15 | 4.5 | 13.5 |
| C15 | 4.5 | 7 | 6 | 6 | 2 | 2.5 | 11 | 16.5 | 5 | 16.5 |
| D18 | 5 | 7.5 | 7 | 7 | 2 | 2.5 | 12 | 20 | 5.5 | 20 |
| E21 | 6 | 9 | 8 | 8 | 3 | 3 | 13.5 | 25 | 6.5 | 25 |
| F24 | 7.5 | 12 | 9 | 9 | 3.5 | 3.5 | 16 | 28 | 7.5 | 28 |
| G27 | 8.5 | 14 | 10 | 10 | 3.5 | 3.5 | 18 | 30 | 9 | 30 |
| H30 | 10 | 15 | 12 | 12 | 4 | 4 | 20 | 34 | 11.5 | 34 |

Figure 3A:
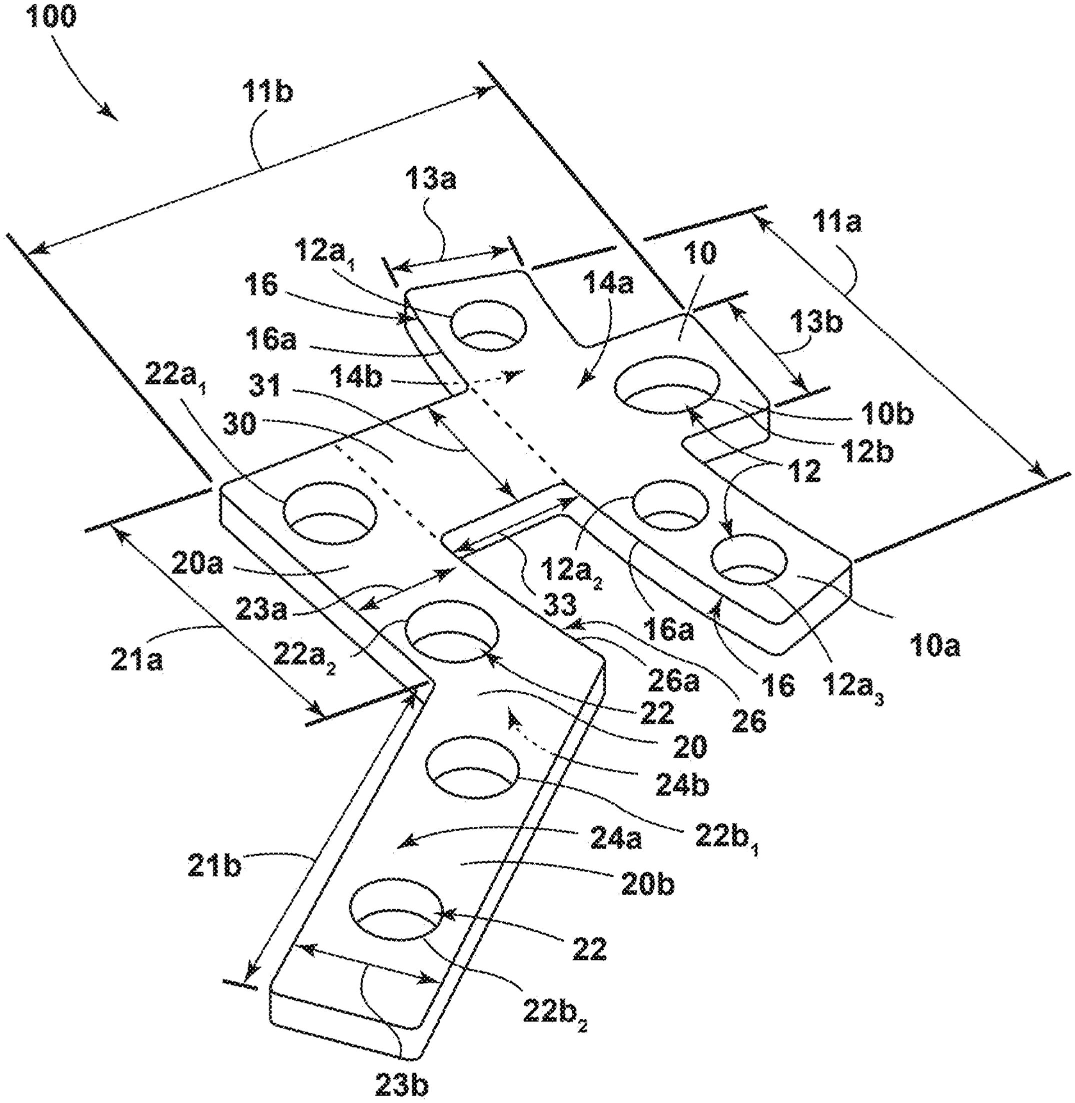
FIG. 3A is a perspective view of an implant device with epiphyseal and metaphyseal tibial plate sections and a ligament, according to another embodiment of the disclosure.
Figure 3B:
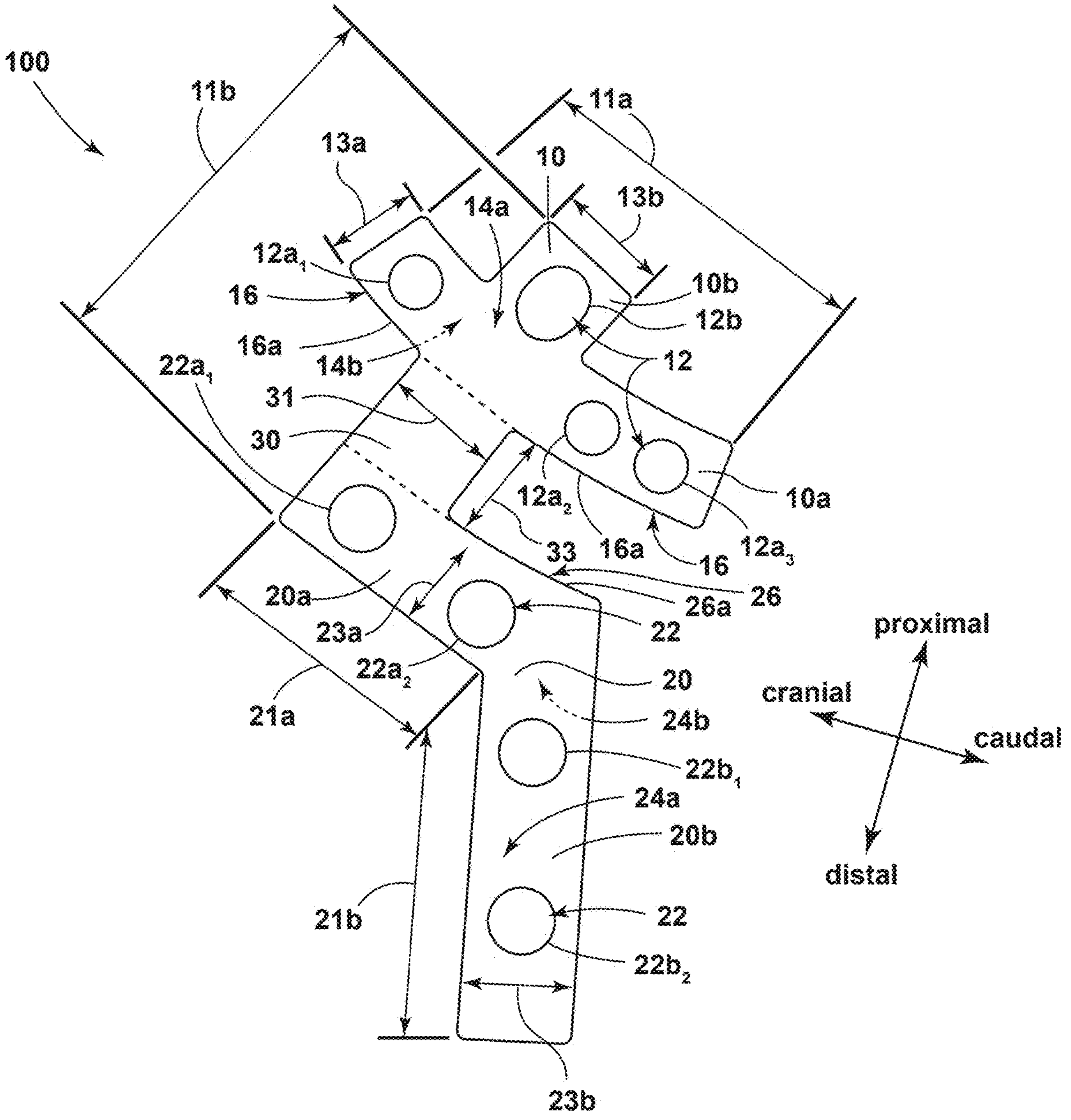
FIG. 3B is a top plan view of the implant device of FIG. 3A.

Referring now to FIGS. 3A and 3B, another embodiment of an implant device 100 is depicted in exemplary form. The implant device 100 of FIGS. 3A and 3B is similar to the implant device of FIGS. 1A-1E with like-numbered elements having substantially the same structure and function, unless otherwise noted. The primary difference is that the implant device 100 of FIGS. 3A and 3B possesses a cranial portion 20*a* of the metaphyseal tibial plate section 20 that includes a cut-adjacent curvilinear surface 26 configured to be positioned adjacent to the curvilinear cut 150 (in addition to the curvilinear portion 10*a* of the epiphyseal tibial plate section 10, with its cut-adjacent curvilinear surface 16). Further, according to some embodiments, the cut-adjacent curvilinear surface 26 can comprise a plate radius 26*a* that is within ±25% of the curvilinear cut radius 150*a* of the curvilinear cut 150 (see FIGS. 2A-2C, described in further detail above). In embodiments, the plate radius 26*a* of the cut-adjacent curvilinear surface 26 of the metaphyseal tibial plate section 20, particularly its cranial portion 20*a*, is within ±25%, 20%, 15%, 10%, 5%, or even 1% of the curvilinear cut radius 150*a*. In some implementations, the plate radius 26*a* of the cut-adjacent curvilinear surface 26 of the cranial portion 20*a* is within ±25%, 20%, 15%, 10%, 5%, or even 1% of the plate radius 16*a* of the curvilinear portion 10*a*. In embodiments, the plate radius 26*a* of the cut-adjacent curvilinear surface 26 can range from 10 mm to 30 mm, e.g., 10 mm, 12 mm, 14 mm, 16 mm, 18 mm, 20 mm, 22 mm, 24 mm, 26 mm, 28 mm, 30 mm, or any radius value between the foregoing. In general, the foregoing configurations relate to the shape of the metaphyseal tibial plate section 20, particularly the cranial portion 20*a* with its cut-adjacent curvilinear surface 26, that generally matches the shape of the curvilinear cut 150 (and the shape of cut-adjacent curvilinear surface 16 of the epiphyseal tibial plate section 10, in some embodiments), including its radius 150*a*, to ensure a uniform distribution of stress and an optimal reinforcement between the epiphyseal and metaphyseal tibial fragments 110, 120.

Figure 4A:
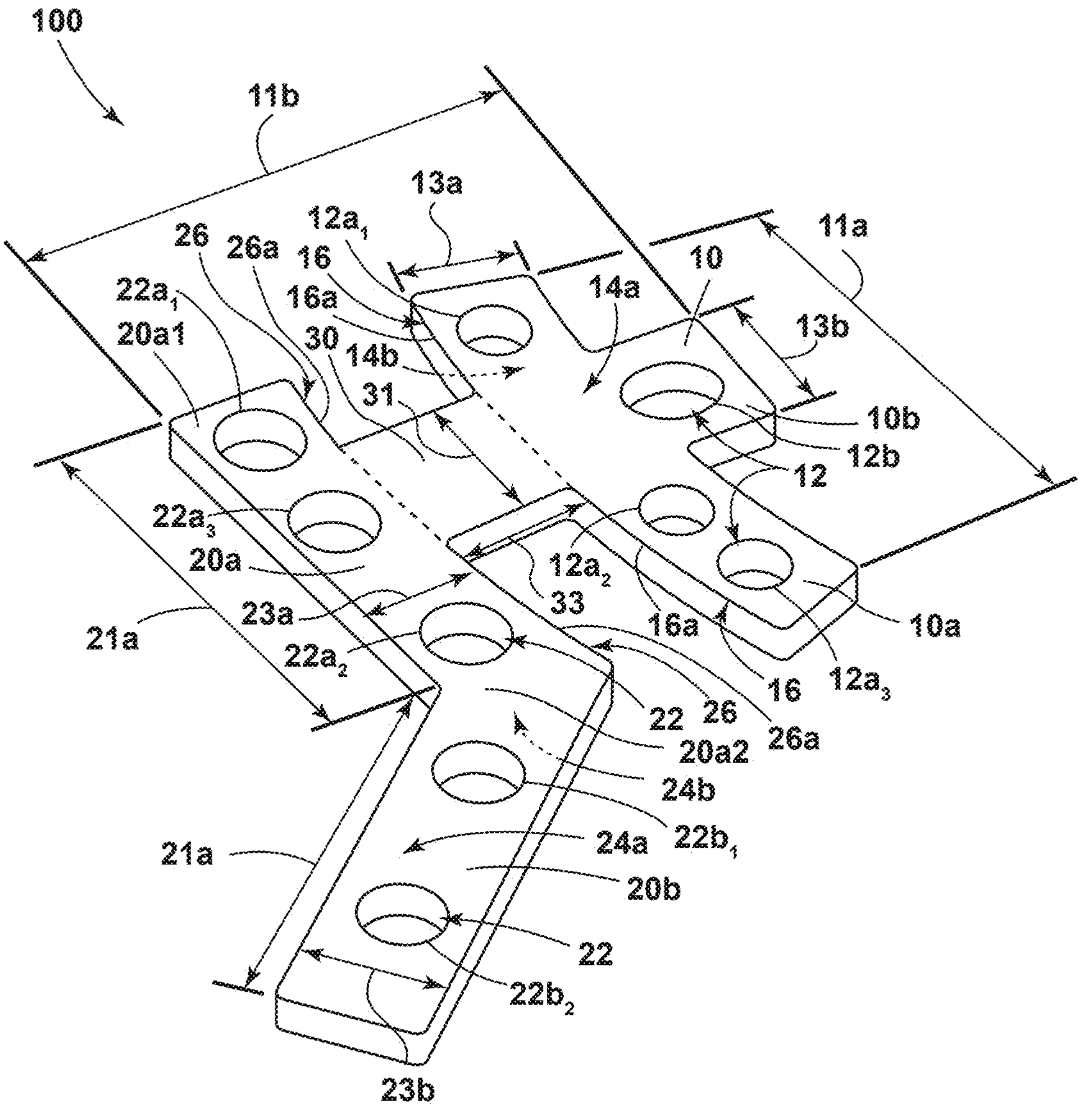
FIG. 4A is a perspective view of an implant device with epiphyseal and metaphyseal tibial plate sections and a ligament, according to another embodiment of the disclosure.
Figure 4B:
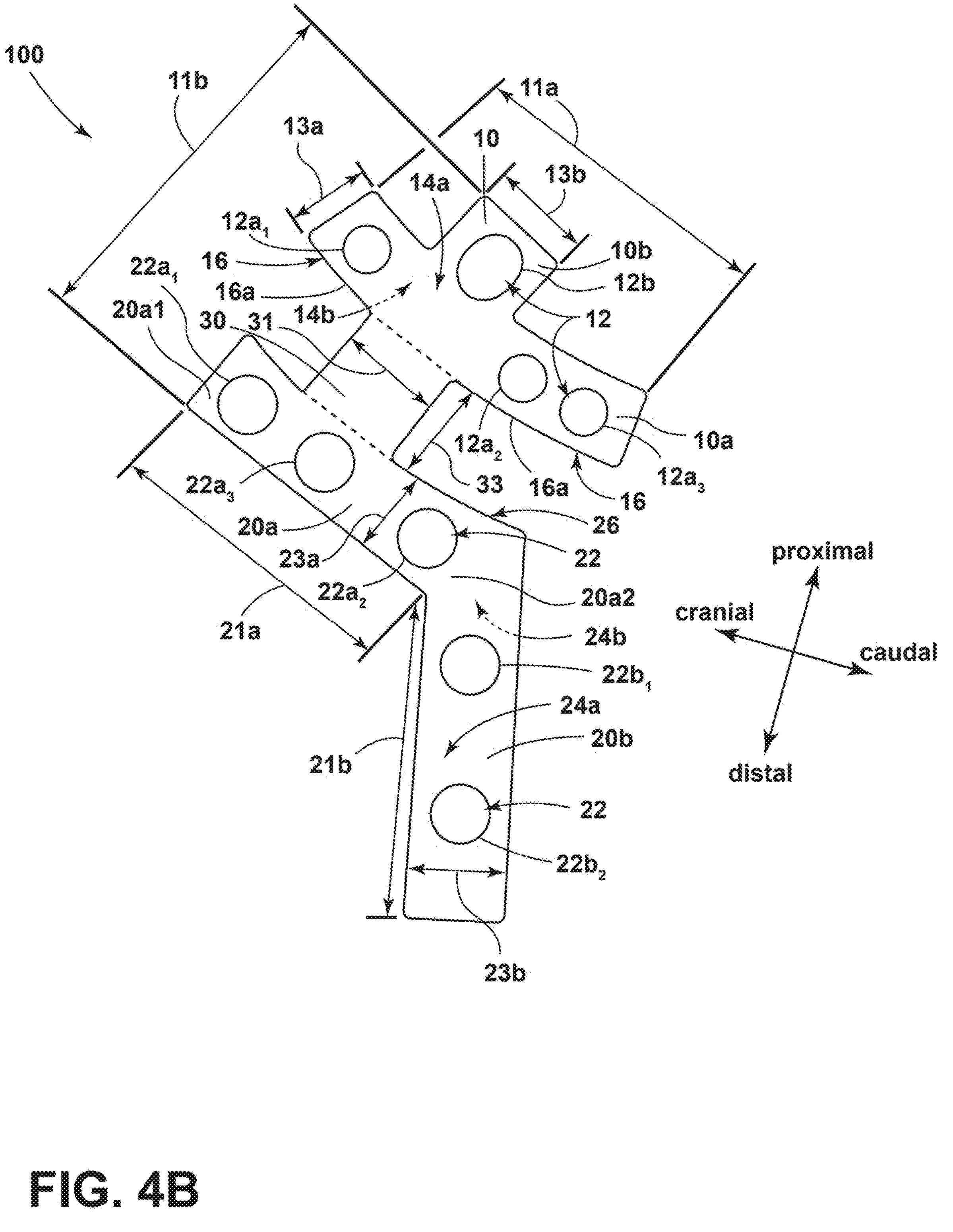
FIG. 4B is a top plan view of the implant device of FIG. 4A.

Referring now to FIGS. 4A and 4B, another embodiment of an implant device 100 is depicted in exemplary form. The implant device 100 of FIGS. 4A and 4B is similar to the implant device of FIGS. 3A and 3B with like-numbered elements having substantially the same structure and function, unless otherwise noted. The primary difference is that the implant device 100 of FIGS. 4A and 4B has a cranial portion 20*a* of the metaphyseal tibial plate section 20 that comprises a metaphyseal cranial segment 20*a*1 extending cranially and perpendicular to the ligament 30 and a metaphyseal caudal segment 20*a*2 that extends caudally and perpendicular to the ligament 30. Each of the metaphyseal cranial segment 20*a*1 and metaphyseal caudal segment 20*a*2 has a cut-adjacent curvilinear surface 26 with a plate radius 26*a*. According to some embodiments, the cranial portion 20*a* of the implant device 100 depicted in exemplary form in FIGS. 4A and 4B can include an additional screw hole 22$a_3$ located between screw holes 22$a_1$ and 22$a_2$ and distally from the ligament 30, the screw hole 22$a_3$ configured to accept a bone screw 180 to secure the plate section 20 to the metaphyseal tibial fragment 120. Further, according to some implementations, the implant device 100 of FIGS. 4A and 4B, particularly as inclusive of metaphyseal cranial and caudal segments 20*a*1 and 20*a*2, respectively, and working in conjunction with the curvilinear portion 10*a* is configured to ensure a uniform distribution of stress and an optimal reinforcement between the epiphyseal and metaphyseal tibial fragments 110, 120.

Aspect 1. An implant device for a tibial plateau leveling osteotomy is provided that includes: an epiphyseal tibial plate section comprising at least three screw holes, a bone-contacting surface and an upper surface, each screw hole running between the bone-contacting and upper surfaces and configured to accept a bone screw to secure the epiphyseal plate section to an epiphyseal tibial bone fragment; a metaphyseal tibial plate section comprising at least three screw holes, a bone-contacting surface and an upper surface, each screw hole running between the bone-contacting and upper surfaces and configured to accept a bone screw to secure the metaphyseal plate section to a metaphyseal tibial bone fragment; and a ligament joining the tibial plate sections and configured to span a curvilinear tibial cut from a tibial plateau leveling osteotomy, wherein the curvilinear cut separates the epiphyseal and metaphyseal tibial bone fragments. Each of the metaphyseal and epiphyseal tibial plate sections and the ligament comprises an implant grade alloy. The epiphyseal tibial plate section comprises a curvilinear portion and a proximal portion, the curvilinear portion oriented perpendicular to the ligament and comprising a cut-adjacent curvilinear surface configured to be positioned adjacent to the curvilinear cut, and the proximal portion is perpendicular and extending proximally to the curvilinear portion. Further the metaphyseal tibial plate section comprises an elongated distal portion and a cranial portion, the cranial portion oriented cranially to the distal portion and perpendicular to the ligament, and the distal portion extending distally from the cranial portion. In addition, each of the tibial plate sections and the ligament comprises a width that is substantially uniform, and each of the width of the ligament and a width of the proximal portion is greater than a width of each of the curvilinear portion, the elongated distal portion and the cranial portion.

Aspect 2. The implant device of Aspect 1, wherein the proximal portion has one screw hole and the curvilinear portion comprises at least three screw holes.

Aspect 3. The implant device of Aspect 2, wherein two of the screw holes of the curvilinear portion are located caudally from the ligament and one of the screw holes of the curvilinear portion is located cranially from the ligament.

Aspect 4. The implant device of Aspect 2, wherein the at least three screw holes of the curvilinear portion comprises a first screw hole positioned cranial to the ligament, a second screw hole positioned caudal to the ligament, and a third screw hole positioned caudal to the second screw hole, wherein the first and third screw holes are oriented substantially normal to the upper and bone-contacting surfaces, and further wherein the second screw hole is oriented both proximally and caudally 5-15° from normal to the upper and bone-contacting surfaces.

Aspect 5. The implant device of Aspect 2, wherein the one screw hole of the proximal portion is elongated toward the ligament and oriented substantially normal to the upper and bone-contacting surfaces.

Aspect 6. The implant device of Aspect 1, wherein the cranial portion has two screw holes and the elongated distal portion comprises at least two screw holes.

Aspect 7. The implant device of Aspect 6, wherein the two screw holes of the cranial portion comprises a first screw hole distal from the ligament and a second screw hole caudal from the first screw hole, the first screw hole oriented substantially normal to the upper and bone-contacting surfaces and the second screw hole oriented caudally 5-15° from normal to the upper and bone-contacting surfaces.

Aspect 8. The implant device of Aspect 6, wherein the at least two screw holes of the elongated distal portion comprises a first screw hole distal from the cranial portion and a second screw hole distal from the first screw hole, the first screw hole oriented caudally 5-15° from normal to the upper and bone-contacting surfaces and the second screw hole oriented substantially normal to the upper and bone-contacting surfaces.

Aspect 9. The implant device of Aspect 1, wherein the cut-adjacent curvilinear surface of the epiphyseal tibial plate section generally matches a shape of the curvilinear cut and is configured for alignment along the curvilinear cut.

Aspect 10. An implant device for a tibial plateau leveling osteotomy is provided that includes: an epiphyseal tibial plate section comprising at least three screw holes, a bone-contacting surface and an upper surface, each screw hole running between the bone-contacting and upper surfaces and configured to accept a bone screw to secure the epiphyseal plate section to an epiphyseal tibial bone fragment; a metaphyseal tibial plate section comprising at least three screw holes, a bone-contacting surface and an upper surface, each screw hole running between the bone-contacting and upper surfaces and configured to accept a bone screw to secure the metaphyseal plate section to a metaphyseal tibial bone fragment; and a ligament joining the tibial plate sections and configured to span a curvilinear tibial cut from a tibial plateau leveling osteotomy, wherein the curvilinear cut separates the epiphyseal and metaphyseal tibial bone fragments. Each of the metaphyseal and epiphyseal tibial plate sections and the ligament comprises an implant grade alloy. Further, the epiphyseal tibial plate section comprises a curvilinear portion and a proximal portion, the curvilinear portion oriented perpendicular to the ligament and comprising a cut-adjacent curvilinear surface configured to be positioned adjacent to the curvilinear cut, and the proximal portion is perpendicular and extending proximally to the curvilinear portion. In addition, the metaphyseal tibial plate section comprises an elongated distal portion and a cranial portion, the cranial portion comprising a cut-adjacent curvilinear surface configured to be positioned adjacent to the curvilinear cut and oriented cranially relative to the distal portion and perpendicular to the ligament, and the distal portion extending distally from the cranial portion. Further, each of the tibial plate sections and the ligament comprises a width that is substantially uniform, and each of the width of the ligament and a width of the proximal portion is greater than a width of each of the curvilinear portion, the elongated distal portion and the cranial portion.

Aspect 11. The implant device of Aspect 10, wherein the proximal portion has one screw hole and the curvilinear portion comprises at least three screw holes.

Aspect 12. The implant device of Aspect 11, wherein two of the screw holes of the curvilinear portion are located caudally from the ligament and one of the screw holes of the curvilinear portion is located cranially from the ligament.

Aspect 13. The implant device of Aspect 11, wherein the at least three screw holes of the curvilinear portion comprises a first screw hole positioned cranial to the ligament, a second screw hole positioned caudal to the ligament, and a third screw hole positioned caudal to the second screw hole, wherein the first and third screw holes are oriented substantially normal to the upper and bone-contacting surfaces, and further wherein the second screw hole is oriented both proximally and caudally 5-15° from normal to the upper and bone-contacting surfaces.

Aspect 14. The implant device of Aspect 11, wherein the one screw hole of the proximal portion is elongated in the direction of the ligament and oriented substantially normal to the upper and bone-contacting surfaces.

Aspect 15. The implant device of Aspect 10, wherein the cranial portion has two screw holes and the elongated distal portion comprises at least two screw holes.

Aspect 16. The implant device of Aspect 15, wherein the two screw holes of the cranial portion comprises a first screw hole distal from the ligament and a second screw hole caudal from the first screw hole, the first screw hole oriented substantially normal to the upper and bone-contacting surfaces and the second screw hole oriented caudally 5-15° from normal to the upper and bone-contacting surfaces.

Aspect 17. The implant device of Aspect 15, wherein the at least two screw holes of the elongated distal portion comprises a first screw hole distal from the cranial portion and a second screw hole distal from the first screw hole, the first screw hole oriented caudally 5-15° from normal to the upper and bone-contacting surfaces and the second screw hole oriented substantially normal to the upper and bone-contacting surfaces.

Aspect 18. The implant device of Aspect 10, wherein each of the cut-adjacent curvilinear surfaces of the epiphyseal and metaphyseal tibial plate sections, respectively, generally matches a shape of the curvilinear cut and is configured for alignment along the curvilinear cut.

Aspect 19. An implant device for a tibial plateau leveling osteotomy is provided that includes: an epiphyseal tibial plate section comprising at least three screw holes, a bone-contacting surface and an upper surface, each screw hole running between the bone-contacting and upper surfaces and configured to accept a bone screw to secure the epiphyseal plate section to an epiphyseal tibial bone fragment; a metaphyseal tibial plate section comprising at least three screw holes, a bone-contacting surface and an upper surface, each screw hole running between the bone-contacting and upper surfaces and configured to accept a bone screw to secure the metaphyseal plate section to a metaphyseal tibial bone fragment; and a ligament joining the tibial plate sections and configured to span a curvilinear tibial cut from a tibial plateau leveling osteotomy, wherein the curvilinear cut separates the epiphyseal and metaphyseal tibial bone fragments. Each of the metaphyseal and epiphyseal tibial plate sections and the ligament comprises an implant grade alloy. Further, the epiphyseal tibial plate section comprises a curvilinear portion and a proximal portion, the curvilinear portion oriented perpendicular to the ligament and comprising a cut-adjacent curvilinear surface configured to be positioned adjacent to the curvilinear cut, and the proximal portion is perpendicular and extending proximally to the curvilinear portion. In addition, the metaphyseal tibial plate section comprises an elongated distal portion and a cranial portion, the cranial portion comprising a cut-adjacent curvilinear surface configured to be positioned adjacent to the curvilinear cut and oriented cranially to the distal portion and perpendicular to the ligament, and the distal portion extending distally from the cranial portion. Further, each of the tibial plate sections and the ligament comprises a width that is substantially uniform, and each of the width of the ligament and a width of the proximal portion is greater than a width of each of the curvilinear portion, the elongated distal portion and the cranial portion. Also, the cranial portion of the metaphyseal tibial plate section has at least two screw holes and comprises a metaphyseal cranial segment extending cranially and perpendicular to the ligament and a metaphyseal caudal segment extending caudally and perpendicular to the ligament.

Aspect 20. The implant device of Aspect 19, wherein each of the cut-adjacent curvilinear surfaces of the curvilinear and cranial portions, respectively, generally matches a shape of the curvilinear cut and is configured for alignment along the curvilinear cut.

Although multiple embodiments of the TPLO implant device of the present disclosure have been illustrated in the accompanying Drawings and described in the foregoing Detailed Description, it should be understood that the present disclosure is not limited to the disclosed embodiments. Rather, the slim tibial plateau leveling osteotomy implant device is also capable of numerous rearrangements (e.g., implant devices with epiphyseal and metaphyseal tibial plate sections having multiple sections, some or all in a curvilinear shape; implant devices with ligaments formed in a mesh to join the tibial plate sections while retaining visibility to the curvilinear cut below, etc.), modifications (e.g., as configured for left or right foreleg tibial bone fragments, left or right hind tibial bone fragments), and/or substitutions without departing from the present disclosure that has been set forth and defined within the following claims.

What is claimed is:

1. An implant device for a tibial plateau leveling osteotomy, comprising:

an epiphyseal tibial plate section comprising at least three screw holes, a bone-contacting surface and an upper surface, each screw hole running between the bone-contacting and upper surfaces and configured to accept a bone screw to secure the epiphyseal plate section to an epiphyseal tibial bone fragment;

a metaphyseal tibial plate section comprising at least three screw holes, a bone-contacting surface and an upper surface, each screw hole running between the bone-contacting and upper surfaces and configured to accept a bone screw to secure the metaphyseal plate section to a metaphyseal tibial bone fragment; and a ligament joining the tibial plate sections and configured to span a curvilinear tibial cut from a tibial plateau leveling osteotomy, wherein the curvilinear cut separates the epiphyseal and metaphyseal tibial bone fragments, wherein each of the metaphyseal and epiphyseal tibial plate sections and the ligament comprises an implant grade alloy, wherein the epiphyseal tibial plate section comprises a curvilinear portion and a proximal portion, the curvilinear portion oriented perpendicular to the ligament and comprising a cut-adjacent curvilinear surface configured to be positioned adjacent to the curvilinear cut, and the proximal portion is perpendicular and extending proximally to the curvilinear portion, wherein the metaphyseal tibial plate section comprises an elongated distal portion and a cranial portion, the cranial portion oriented cranially to the distal portion and perpendicular to the ligament, and the distal portion extending distally from the cranial portion, and further wherein each of the tibial plate sections and the ligament comprises a width that is substantially uniform, and each of the width of the ligament and a width of the proximal portion is greater than a width of each of the curvilinear portion, the elongated distal portion and the cranial portion.

2. The implant device of claim 1, wherein the proximal portion has one screw hole and the curvilinear portion comprises at least three screw holes.

3. The implant device of claim 2, wherein two of the screw holes of the curvilinear portion are located caudally from the ligament and one of the screw holes of the curvilinear portion is located cranially from the ligament.

4. The implant device of claim 2, wherein the at least three screw holes of the curvilinear portion comprises a first screw hole positioned cranial to the ligament, a second screw hole positioned caudal to the ligament, and a third screw hole positioned caudal to the second screw hole, wherein the first and third screw holes are oriented substantially normal to the upper and bone-contacting surfaces, and further wherein the second hole is oriented both proximally and caudally 5-15° from normal to the upper and bone-contacting surfaces.

5. The implant device of claim 2, wherein the one screw hole of the proximal portion is elongated toward the ligament and oriented substantially normal to the upper and bone-contacting surfaces.

6. The implant device of claim 1, wherein the cranial portion has two screw holes and the elongated distal portion comprises at least two screw holes.

7. The implant device of claim 6, wherein the two screw holes of the cranial portion comprises a first screw hole distal from the ligament and a second screw hole caudal from the first screw hole, the first screw hole oriented substantially normal to the upper and bone-contacting surfaces and the second screw hole oriented caudally 5-15° from normal to the upper and bone-contacting surfaces.

8. The implant device of claim 6, wherein the at least two screw holes of the elongated distal portion comprises a first screw hole distal from the cranial portion and a second screw hole distal from the first screw hole, the first screw hole oriented cranially 5-15° from normal to the upper and bone-contacting surfaces and the second screw hole oriented caudally 5-15° from normal to the upper and bone-contacting surfaces.

9. The implant device of claim 1, wherein the cut-adjacent curvilinear surface of the curvilinear portion generally matches a shape of the curvilinear cut and is configured for alignment along the curvilinear cut.

10. An implant device for a tibial plateau leveling osteotomy, comprising:

an epiphyseal tibial plate section comprising at least three screw holes, a bone-contacting surface and an upper surface, each screw hole running between the bone-contacting and upper surfaces and configured to accept a bone screw to secure the epiphyseal plate section to an epiphyseal tibial bone fragment;

a metaphyseal tibial plate section comprising at least three screw holes, a bone-contacting surface and an upper surface, each screw hole running between the bone-contacting and upper surfaces and configured to accept a bone screw to secure the metaphyseal plate section to a metaphyseal tibial bone fragment; and a ligament joining the tibial plate sections and configured to span a curvilinear tibial cut from a tibial plateau leveling osteotomy, wherein the curvilinear cut separates the epiphyseal and metaphyseal tibial bone fragments, wherein each of the metaphyseal and epiphyseal tibial plate sections and the ligament comprises an implant grade alloy, wherein the epiphyseal tibial plate section comprises a curvilinear portion and a proximal portion, the curvilinear portion oriented perpendicular to the ligament and comprising a cut-adjacent curvilinear surface configured to be positioned adjacent to the curvilinear cut, and the proximal portion is perpendicular and extending proximally to the curvilinear portion, wherein the metaphyseal tibial plate section comprises an elongated distal portion and a cranial portion, the cranial portion comprising a cut-adjacent curvilinear surface configured to be positioned adjacent to the curvilinear cut and oriented cranially relative to the distal portion and perpendicular to the ligament, and the distal portion extending distally from the cranial portion, and further wherein each of the tibial plate sections and the ligament comprises a width that is substantially uniform, and each of the width of the ligament and a width of the proximal portion is greater than a width of each of the curvilinear portion, the elongated distal portion and the cranial portion.

11. The implant device of claim 10, wherein the proximal portion has one screw hole and the curvilinear portion comprises at least three screw holes.

12. The implant device of claim 11, wherein two of the screw holes of the curvilinear portion are located caudally from the ligament and one of the screw holes of the curvilinear portion is located cranially from the ligament.

13. The implant device of claim 11, wherein the at least three screw holes of the curvilinear portion comprises a first screw hole positioned cranial to the ligament, a second screw hole positioned caudal to the ligament, and a third screw hole positioned caudal to the second screw hole, wherein the first and third screw holes are oriented substantially normal to the upper and bone-contacting surfaces, and further wherein the second screw hole is oriented both proximally and caudally 5-15° from normal to the upper and bone-contacting surfaces.

14. The implant device of claim 11, wherein the one screw hole of the proximal portion is elongated in the direction of the ligament and oriented substantially normal to the upper and bone-contacting surfaces.

15. The implant device of claim 10, wherein the cranial portion has two screw holes and the elongated distal portion comprises at least two screw holes.

16. The implant device of claim 15, wherein the two screw holes of the cranial portion comprises a first screw hole distal from the ligament and a second screw hole caudal from the first screw hole, the first screw hole oriented substantially normal to the upper and bone-contacting surfaces and the second screw hole oriented caudally 5-15° from normal to the upper and bone-contacting surfaces.

17. The implant device of claim 15, wherein the at least two screw holes of the elongated distal portion comprises a first screw hole distal from the cranial portion and a second screw hole distal from the first screw hole, the first screw hole oriented cranially 5-15° from normal to the upper and bone-contacting surfaces and the second screw hole oriented caudally 5-15° from normal to the upper and bone-contacting surfaces.

18. The implant device of claim 10, wherein each of the cut-adjacent curvilinear surfaces of the curvilinear and cranial portions, respectively, generally matches a shape of the curvilinear cut and is configured for alignment along the curvilinear cut.

19. An implant device for a tibial plateau leveling osteotomy, comprising:

an epiphyseal tibial plate section comprising at least three screw holes, a bone-contacting surface and an upper surface, each screw hole running between the bone-contacting and upper surfaces and configured to accept a bone screw to secure the epiphyseal plate section to an epiphyseal tibial bone fragment;

a metaphyseal tibial plate section comprising at least three screw holes, a bone-contacting surface and an upper surface, each screw hole running between the bone-contacting and upper surfaces and configured to accept a bone screw to secure the metaphyseal plate section to a metaphyseal tibial bone fragment; and a ligament joining the tibial plate sections and configured to span a curvilinear tibial cut from a tibial plateau leveling osteotomy, wherein the curvilinear cut separates the epiphyseal and metaphyseal tibial bone fragments, wherein each of the metaphyseal and epiphyseal tibial plate sections and the ligament comprises an implant grade alloy, wherein the epiphyseal tibial plate section comprises a curvilinear portion and a proximal portion, the curvilinear portion oriented perpendicular to the ligament and comprising a cut-adjacent curvilinear surface configured to be positioned adjacent to the curvilinear cut, and the proximal portion is perpendicular and extending proximally to the curvilinear portion, wherein the metaphyseal tibial plate section comprises an elongated distal portion and a cranial portion, the cranial portion comprising a cut-adjacent curvilinear surface configured to be positioned adjacent to the curvilinear cut and oriented cranially to the distal portion and perpendicular to the ligament, and the distal portion extending distally from the cranial portion, wherein each of the tibial plate sections and the ligament comprises a width that is substantially uniform, and each of the width of the ligament and a width of the proximal portion is greater than a width of each of the curvilinear portion, the elongated distal portion and the cranial portion, and further wherein the cranial portion of the metaphyseal tibial plate section has at least two screw holes and comprises a metaphyseal cranial segment extending cranially and perpendicular to the ligament and a metaphyseal caudal segment extending caudally and perpendicular to the ligament.

20. The implant device of claim 19, wherein each of the cut-adjacent curvilinear surfaces of the curvilinear and cranial portions, respectively, generally matches a shape of the curvilinear cut and is configured for alignment along the curvilinear cut.

* * * * *